US012673124B2

(12) United States Patent (10) Patent No.: US 12,673,124 B2
Lam et al. (45) Date of Patent: Jul. 7, 2026

(54) SYSTEMS AND METHODS OF PLASMA-DISINFECTING A CHANNEL BY DIRECT PLASMA

(71) Applicant: Plasmatica Ltd., Raanana (IL)

(72) Inventors: Amnon Lam, Givat Oz (IL); Osnat Czhertek, Haifa (IL); Adam Sagiv, Bnei Atarot (IL)

(73) Assignee: Plasmatica Ltd., Raanana (IL)

( * ) Notice: Subject to any disclaimer, the term of this patent is extended or adjusted under 35 U.S.C. 154(b) by 0 days.

(21) Appl. No.: 19/260,344

(22) Filed: Jul. 4, 2025

(65) Prior Publication Data

US 2025/0332305 A1      Oct. 30, 2025

Related U.S. Application Data

(63) Continuation of application No. PCT/IB2024/057790, filed on Aug. 11, 2024.
(Continued)

(51) Int. Cl.
*B01J 19/08*      (2006.01)
*A61L 2/14*      (2006.01)
(Continued)

(52) U.S. Cl.
CPC .................... *A61L 2/14* (2013.01); *A61L 2/24* (2013.01); *A61L 2103/15* (2026.01); *A61L 2202/121* (2013.01)

(58) Field of Classification Search
CPC .......... A61L 2/24; A61L 2/14; A61L 2202/24; H05H 1/2431; H05H 2245/36
(Continued)

(56) References Cited

U.S. PATENT DOCUMENTS 4,321,232 A      3/1982   Bithell
4,801,427 A      1/1989   Jacob
(Continued)

FOREIGN PATENT DOCUMENTS

CN      103585650 A      2/2014
CN      107614023 A      1/2018
(Continued)

OTHER PUBLICATIONS

PCT search report for PCT/IB2024/057790 which mailed on Feb. 14, 2023.
(Continued)

*Primary Examiner* — Monzer R Chorbaji
(74) *Attorney, Agent, or Firm* — Momentum IP Ltd.; Marc Van Dyke

(57)      ABSTRACT

A disinfection system and methods thereof for generating direct plasma at sub-atmospheric pressure to treat an inner surface of a channel of a surgical device. The method provides for inserting the surgical device into a gas-sealable enclosure; positioning an elongate discharge electrode within the channel such that the elongate discharge electrode coaxially spans at least a lengthwise majority of the channel to define an annular ignition-region within the channel; electrically coupling a collecting electrode with the conductive circumscribing sleeve of the surgical device; gas-sealing the gas-sealable enclosure; reducing a pressure of the annular ignition-region containing ambient air to a sub-atmospheric pressure; and. electrically igniting the ambient air of the annular ignition-region of the channel by applying an electrical potential difference to produce a longitudinal plasma cloud sufficient to disinfect.

20 Claims, 6 Drawing Sheets

Related U.S. Application Data

(60) Provisional application No. 63/518,636, filed on Aug. 10, 2023.

(51) Int. Cl.
| | | |
|---|---|---|
| *A61L 2/24* | (2006.01) | |
| *A61L 9/00* | (2006.01) | |
| *A61L 103/15* | (2026.01) | |

(58) Field of Classification Search
USPC ................................ 422/4, 186.05, 292, 305
See application file for complete search history.

(56) References Cited

U.S. PATENT DOCUMENTS

| | | | | |
|---|---|---|---|---|
| 5,882,589 | A | 3/1999 | Mariotti | |
| 6,342,187 | B1 | 1/2002 | Jacob | |
| 8,475,451 | B2 | 7/2013 | Cho | |
| 10,251,963 | B2 | 4/2019 | Vinteler | |
| 10,265,116 | B2 | 4/2019 | Stieber | |
| 10,933,151 | B2 | 3/2021 | Nelson | |
| 11,253,620 | B2 | 2/2022 | Golkowski | |
| 11,541,140 | B2 | 1/2023 | Hancock | |
| 12,262,877 | B2 | 4/2025 | Sagiv | |
| 2004/0037736 | A1* | 2/2004 | Perruchot | A61L 2/24 |
| | | | | 422/4 |
| 2011/0116967 | A1 | 5/2011 | Roy | |
| 2013/0230426 | A1 | 9/2013 | Popot | |
| 2020/0316239 | A1 | 10/2020 | Davis | |
| 2022/0001056 | A1 | 1/2022 | Truica-Marasescu | |
| 2022/0240770 | A1 | 8/2022 | Sagiv | |
| 2023/0201390 | A1 | 6/2023 | Kim | |
| 2023/0372567 | A1 | 11/2023 | Hancock | |
| 2024/0207473 | A1 | 6/2024 | Lim | |

FOREIGN PATENT DOCUMENTS

| | | | |
|---|---|---|---|
| EP | 1477188 | A1 | 11/2004 |
| EP | 2471348 | A1 | 7/2012 |
| EP | 4135782 | A1 | 2/2023 |
| JP | 3813586 | B2 | 8/2006 |
| WO | 00/54819 | A1 | 9/2000 |
| WO | 00/72889 | A1 | 12/2000 |
| WO | 2009/067682 | A2 | 5/2009 |
| WO | 2011/055113 | A1 | 5/2011 |
| WO | 2012/016329 | A1 | 2/2012 |
| WO | 2012/018891 | A2 | 2/2012 |
| WO | 2019/175063 | A1 | 9/2019 |
| WO | 2022/106215 | A1 | 5/2022 |

OTHER PUBLICATIONS

PCT search opinion for PCT/IB2024/057790 which mailed on Feb. 14, 2023.

Brandenburg R, Becker KH, Weltmann KD. "Barrier Discharges in Science and Technology Since 2003: A Tribute and Update." Plasma Chem Plasma Process. 2023;43(6):1303-1334.

Fiebrandt M, Lackmann JW, Stapelmann K. "From patent to product? 50 years of low-pressure plasma sterilization." Plasma Process Polym. 2018;15:e1800139.

Northage N, Shvalya V, Modic M, Juergens T, Eschborn S, Horsburgh MJ, Walsh JL. "Evaluation of plasma activated liquids for the elimination of mixed species biofilms within endoscopic working channels." Sci Rep. 2024;14:28593.

Northage N, Simon S, Shvalya V, Modic M, Juergens T, Eschborn S, Horsburgh MJ, Walsh JL. "Efficient endoscope inner channel surface disinfection using a two-step atmospheric pressure plasma treatment." Appl Surf Sci. 2023;623:156936.

Sakudo A, Yagyu Y, Onodera T. "Disinfection and Sterilization Using Plasma Technology: Fundamentals and Future Perspectives for Biological Applications." Int J Mol Sci. 2019;20(20):5216.

Van den Berg D, Asker D, Awad TS, Lavielle N, Hatton BD. "Mechanical deformation of elastomer medical devices can enable microbial surface colonization." Sci Rep. 2023;13:7691.

* cited by examiner

SYSTEMS AND METHODS OF PLASMA-DISINFECTING A CHANNEL BY DIRECT PLASMA

CROSS-REFERENCE TO RELATED APPLICATIONS

PCT/IB2024/057790 filed on Aug. 11, 2024 is incorporated herein by reference in its entirety. U.S. Provisional Patent Application No. 63/518,636, filed Aug. 10, 2023 is incorporated herein by reference in its entirety.

FIELD OF THE INVENTION

The present invention relates to a system and method of generating direct plasma within a channel of a surgical device such as a scope. More specifically, the systems and methods described herein relate to an enclosure for plasma disinfecting the inner surface of a channel under sub-atmospheric pressure.

BACKGROUND OF THE INVENTION

Surgical scopes such as duodenoscopes, endoscopes and gastroscopes, typically have long and narrow lumens which function as a working channel, as well as deep and/or detailed crevices (e.g., endoscope elevator) used for control of instruments at a distal end. Microorganisms and infectious agents are known to grow on the interior surface of these channels or crevices extending from these channels. Over the years, there has been development of detailed guidance for processing scopes in the healthcare setting after each use, in order to minimize risk of transmission of these organisms between patients. The processing typically involves long and rigorous cleaning efforts, exposing the outside surfaces and surfaces of the channels to scrubbing and liquid chemical sterilant solutions, while often requiring additional stages to remove trace amounts of residue harmful chemicals.

Despite many efforts to sterilize, brush, flush or apply liquid disinfectant to remove microorganisms, surgical scopes, and specifically their long and narrow channels or detailed crevices, have been suspected in transmission of infection, including some of the more fatal bacterial infections including Methicillin-Resistant Staphylococcus Aureus (MRSA), Clostridium difficile and *Escherichia coli* (*E. coli*). Thus, microbial colonization may form in visually undetectable, mechanically deformed, and damaged areas of the working channel (Van den Berg, 2023).

Recent research has demonstrated that plasma, can effectively inactivate microbiological pathogens such bacteria, fungus, and viruses (Sakudo, 2019). In recent years, there has been concentrated efforts to try and reduce trace microorganisms by applying plasma to the inner surface of these channels. PCT Patent Application Publication No. WO2022106215 discloses an energy-based disinfection systems where an electric field is concentrated at a probe tip or distal nozzle which is passed through a channel to treat its inner gas (e.g., ambient air). Ionizable gas or air is typically delivered to the channel and the probe tip or nozzle generates an electric field to ionize the gas and produce plasma at the tip. The probe tip is subsequently moved lengthwise along the channel to apply plasma at different locations along the channel. PCT Patent Application Publication No. WO2019175063 discloses an apparatus for sterilizing surgical scoping devices using a probe tip having an outlet for releasing plasma from the internal volume where it is generated, so that the generated plasma flows out of the distal open end of the second electrode to contact an inner channel surface of the surgical scoping devices in which the probe tip is inserted.

Despite the costly and time-consuming alternatives, to date, no methods involving plasma treatment of these surgical device channels have been approved for use in treatment of microorganisms in surgical scopes. It would be desirable to provide additional or improved systems and methods of using plasma for treatment of working channels to reduce the microbial load of infectious agents thereby reducing risk of transmission.

SUMMARY OF THE INVENTION

The present invention aims to overcome these problems and meet these needs in the healthcare system and specifically to reduce healthcare-associated infections. The present disclosure is directed to systems, methods and devices which disinfect inner surfaces of channels of surgical devices and internal cavities by employing direct plasma produced under sub-atmospheric pressure.

According to a first aspect of the invention, there is provided a method of disinfecting an inner surface of a channel (e.g., working channel) of a surgical device (e.g., scope), said channel containing a gas (e.g., ambient air) and said surgical device having a conductive circumscribing sleeve surrounding the channel. The method includes: inserting the surgical device into a gas-sealable enclosure such as a chamber; positioning an elongate discharge electrode, for example, one which includes an insulated dielectric outer layer, within the channel such that the elongate discharge electrode coaxially spans at least a lengthwise majority of the channel to define an annular ignition-region within the channel. The method further includes electrically coupling (for example, by contacting) a collecting electrode with the conductive circumscribing sleeve of the surgical device, for example, by electrically coupling between the collecting electrode and an electrically conductive extension from the conductive circumscribing sleeve (such as a suction port of an endoscope). The method further includes gas-sealing the gas-sealable enclosure and reducing a pressure of the annular ignition-region containing gas (e.g., ambient air) to a sub-atmospheric pressure; and electrically igniting the gas (e.g., ambient air) of the annular ignition-region of the channel by applying an electrical potential difference between the electrodes to produce a longitudinal plasma cloud.

In some embodiments, wherein positioning an elongate discharge electrode within the working channel involves a motor associated with the elongate discharge electrode for advancing the elongate discharge electrode through a length of the working channel.

In some embodiments, the elongate discharge electrode and the collecting electrode with the conductive circumscribing sleeve of the surgical device provide a closed circuit. In some embodiments, applying an electrical potential difference results in a radially extending plasma cloud extending from the elongate discharge electrode and towards the inner surface of the channel. In preferred embodiments, the longitudinal plasma cloud is sufficient to disinfect the inner surface of the channel, such as a working channel.

In some embodiments, the method further includes gas-sealing the gas-sealable enclosure by sealing a gas-sealable opening (or door) of the enclosure, said gas-sealable chamber further having a gas-tight utility port in fluid communication with a negative pressure pump. In some embodiments, reducing a pressure of the annular ignition-region containing gas (e.g., ambient air) to a sub-atmospheric pressure involves activation of a negative pressure pump outside of the gas-sealable chamber.

In some embodiments, the method further includes reducing a pressure of the annular ignition-region containing a gas (e.g., ambient air) to a sub-atmospheric pressure by reducing the pressure of the gas-sealable chamber to a sub-atmospheric pressure. In some embodiments, reducing the pressure of the gas-sealable chamber is to pressure of less than 200 mbar. In some embodiments, reducing the pressure of the gas-sealable chamber is to pressure of less than 100 mbar. In some embodiments, reducing a pressure is to a pressure of less than 50 mbar. In some embodiments, reducing a pressure is to a pressure of less than 20 mbar.

In some embodiments, reducing a pressure of the annular ignition-region is periodically reducing a pressure while allowing a fresh source of ambient air or gas to enter between the periodic reducing of pressure.

In some embodiments, reducing a pressure of the annular ignition-region comprises removing residue (e.g., gas or liquid), towards a negative pressure pump. Removing the residue may be into a collecting canister. This step may be performed prior to or after igniting the gas in the channel. In some examples, the negative pressure pump and a collecting canister is further configured to remove residual liquid remaining from a previous cleaning method, unrelated to the present method, and prior to electrically igniting the ambient air of the annular ignition-region. In a particularly preferred embodiment, a high-pressure negative pressure may be applied to remove a liquid residue from the channel which is present due to a previous cleaning process and prior to electrically ionizing the ambient air. This may be possible by use of a powerful vacuum pump or alternatively by using the volume of the collecting canister to apply a negative pressure which is contained and subsequently released suddenly in a burst of high negative pressure into the enclosure.

In some examples, the residue may be removed through a filter. This residue may further be qualified to affect a decision on subsequent number or type of treatment steps.

In some embodiments, the ionized gas is removed to some extent post treatment from the enclosure.

Once the pressure is reduced, the method includes electrically igniting the gas (e.g., ambient air) of the annular ignition-region of the channel by applying an electrical potential difference sufficient to disinfect or reduce a presence of living microorganisms on the inner surface of the channel. Prior to igniting the gas, the path between the elongate discharge electrode and the inner surface of the channel should be free from any highly electrically conductive material.

In some embodiments, igniting the gas (e.g., ambient air) is by applying an electrical potential difference to the elongate discharge electrode which coaxially spans at least a lengthwise majority of a portion of the working channel. In some embodiments, igniting the gas (e.g., ambient air) is by applying an electrical potential difference to the elongate discharge electrode which coaxially spans the channel in a manner which is substantially contactless with respect to the inner surface of the channel. In some embodiments, igniting the gas (e.g., ambient air) is by applying an electrical potential difference to the elongate discharge electrode which coaxially spans the channel in a manner which may contact an inner surface of the channel while applying a plasma cloud to an opposing inner surface. In some embodiments, applying an electrical potential difference is between a longitudinally static elongate discharge electrode relative to the channel and the conductive circumscribing sleeve for example during a period of time to disinfect the inner surface of the channel.

In some embodiments, applying an electrical potential difference between the elongate discharge electrode and collecting electrodes is for a period of time sufficient to disinfect the inner surface of the working channel. The time period may be less than 20 minutes, less than 15 minutes, less than 10 minutes, less than 8 minutes, less than 6 minutes, less than 4 minutes, or less than 2 minutes. In preferred embodiments, the time period sufficient to disinfect is between 5 and 10 minutes.

Sufficient to disinfect the inner surface of the channel may be a reduction in presence of living microorganisms of at least a 3, 5 or 8 log CFU per cm^2.

In some embodiments, applying an electrical potential difference between the elongate discharge electrode and the conductive circumscribing sleeve is along a coaxial length of a working channel of at least 0.75, 1 or 1.5 meter.

In some embodiments, a surgical device exterior and/or a distal end of the channel or extension thereof is further exposed to ionized molecules from the plasma region by indirect plasma.

In some embodiments, the elongate discharge electrode has a conducting outer-surface which is uninsulated. In preferred embodiments, the elongate discharge electrode has an insulated dielectric outer surface. In some embodiments, electrically igniting the gas (e.g., ambient air) of the annular ignition-region spans at least a lengthwise majority of a proximal half of the working channel or a proximal half of the elongate discharge electrode.

In preferred embodiments, the method further comprises a stage of drying the inner surface of the channel prior to, after electrically igniting the gas (e.g., ambient air) or both. For example, a negative pressure may be applied to the enclosure to reach a target pressure and then a fresh volume of gas may enter via a port in the enclosure. In some embodiments, the method further comprises reintroducing into the working channel a fresh volume of air or gas after electrically igniting the gas (e.g., ambient air). In some embodiments, the method further comprises a step of removing ionized gas out of a chamber via a filter.

In some embodiments, electrically igniting the gas (e.g., ambient air) is without relative longitudinal motion between wire and the working channel. In some embodiments, electrically igniting the gas (e.g., ambient air) of the annular ignition-region of the working channel is sufficient to reduce presence of living microorganisms on the inner surface of the working channel by at least 3, 5 or 8 log CFU per cm^2. In preferred embodiments, electrically igniting the gas (e.g., ambient air) of the annular ignition-region of the working channel is sufficient to reduce the presence of living microorganisms is by at least 8 log reduction in CFU per cm^2.

In some embodiments, the surgical device further comprises a distal end having crevices such as an elevator region and the method further comprises applying to a surgical device tip an additional discharge electrode having a cap shape and adapted to cap an elevator region and electrically igniting gas (e.g., ambient air) to form plasma in an area of the elevator region.

In particularly preferred embodiments, upon completion of treatment, the surgical device is stored in the enclosure until use.

In another aspect, there is provided, a disinfection system for plasma-disinfecting an interior surface of a channel of a surgical device having a conductive circumscribing sleeve surrounding the channel, said disinfection system comprising:

i. a pair of spaced-apart electrodes located on opposite sides of the channel wall, said electrodes configured to apply an ionizing electric field radially and over a lengthwise majority of the elongate discharge electrode ii. a gas-sealable enclosure having a gas-sealable opening (e.g., door) sized to receive a surgical device and one or more gas-tight utility ports spanning a wall of the gas-sealable enclosure, said gas-tight utility ports adapted to a. fluidly connect between a negative pressure source on the outside and an end of a channel on the inside; and b. electrically couple between a power source on the outside and a pair of spaced-apart electrodes on the inside; and iii. a controller configured, when a combination of (i) the gas-sealable enclosure, (ii) the pair of spaced-apart electrodes, and (iii) the channel are in a ready-to-ignite-plasma state, to electrically ignite at least some ambient air to form plasma, so as to disinfect an inner surface of the surgical device.

In yet another aspect, there is provided a disinfection system for plasma-disinfecting an interior surface of a channel of a surgical device having a conductive circumscribing sleeve surrounding the channel such as a working channel of a surgical scope. The disinfection system may include: a chamber or enclosure associated with a negative pressure pump and having a gas-sealable opening or door and one or more gas-tight utility ports; a pair of spaced-apart electrodes located on opposite sides of a channel wall, each member of the pair electrically associated with a power source, e.g., by capacitive coupling, said pair configured to apply an ionizing electric field radially from the elongate discharge electrode and over a lengthwise majority of the elongate discharge electrode; and a controller. The controller may be configured, to electrically ignite at least some gas (e.g., ambient air) to form plasma, so as to disinfect an inner surface of the surgical device. In some embodiments, the controller may be configured to electrically ignite at least some gas (e.g., ambient air) to form plasma, so as to disinfect an inner surface of the surgical device when a combination of the chamber, the two electrodes, and the channel is in a ready-to-ignite-plasma state, to electrically ignite at least some gas to form plasma, so as to disinfect an inner surface of the surgical device. In one embodiment, the controller be configured, to electrically ignite at least some gas (e.g., ambient air) to form plasma, contingent upon a combination of all of the chamber, the plasma generator, and the channel, being in the ready-to-ignite state. In another embodiment, a controller is configured detect that a combination of the chamber, the plasma generator, and the channel are in the ready-to-ignite state prior to electrically igniting at least some gas (e.g., ambient air) to form plasma. In some embodiments, the pair of spaced-apart electrodes located on opposite sides of the channel wall comprise: an elongate discharge electrode having a dielectric exterior and a collecting electrode adapted to electrically associate with a conductive circumscribing portion of the surgical device.

In some embodiments of the disinfection system, the ready-to-ignite state requires all of the following: at least a section of the elongate discharge electrode is disposed within the channel of the surgical device so that the elongate discharge electrode coaxially spans at least a lengthwise majority of the channel to define an annular region within the channel; the collecting electrode is electrically coupled to the conductive circumscribing sleeve of the surgical device; the gas-sealable enclosure is gas-sealed and a negative pressure pump is activated such that said annular region is maintained at a sub-atmospheric pressure.

In another embodiment, the elongate discharge electrode is sized and shaped for longitudinal placement within a working channel and the collecting electrode is adapted to electrically couple with a conductive circumscribing portion of the surgical device.

In another embodiment, the elongate discharge electrode has a length of at least 0.75 meter, 1 meter, or 1.5 meters.

In another embodiment, the elongate discharge electrode is configured to drive a radial electric field towards a conductive circumscribing sleeve of the surgical device.

In another embodiment, the controller is configured to activate the power source for a time period sufficient to cause a reduction of contamination on an inner channel surface. In some embodiments, a controller is further configured to intermittently apply a negative pressure to the channel.

In another embodiment, the one or more gas-tight utility ports spanning a wall of the enclosure are organized on a single adapter.

In some embodiments, a collection chamber is associated with the enclosure and configured to receive liquid residue upon application of negative pressure prior to ignition of plasma.

In another embodiment, the one or more gas-tight utility ports extend through a gas (e.g., ambient air) of the chamber and enable communication between an inner volume of the chamber and a negative pressure pump or gas source.

In another embodiment, the one or more gas-tight utility ports and gas-sealable door provide passage while substantially isolating an inner pressure during treatment. For example, a gas-tight utility port extending through the wall of the enclosure may be configured to release plasma exhaust or waste. This exhaust port may further include a filter or collection canister configured to collect residual by products (e.g., ozone) of the disinfection treatment.

In another embodiment, the one or more gas-tight utility ports comprise a seal dimensioned to sealingly circumscribe an external circumference of a conduit communicating between an inner volume of the chamber and outside the chamber.

In another embodiment, the chamber is configured for multiple use. In another embodiment, the chamber is configured for single use. In another embodiment, the chamber is flexible but includes structural support to maintain an inner volume surrounding the surgical device despite sub-atmospheric pressure applied.

In another embodiment, the plasma generator or pair of electrodes are configured to apply an ionizing electric field over a lengthwise majority of the channel when the system is positioned in a ready-to-ignite state, said ready-to-ignite state requiring all of the following: at least a section of the elongate discharge electrode is disposed within the channel of the surgical device so that the elongate discharge electrode coaxially spans at least a lengthwise majority of the channel to define an annular region within the channel; the collecting electrode is in contact with a region of the conductive circumscribing sleeve of the surgical device; the chamber is gas-sealed and the negative pressure pump is activated such that said annular region is maintained at a sub-atmospheric pressure.

BRIEF DESCRIPTION OF THE DRAWINGS

Embodiments of the invention will now be described by way of example with reference to the accompanying drawings which illustrate several embodiments of the disclosure and together with the description, serve to explain the principles of the disclosure.

FIGS. 4A and 4B illustrate an orthogonal view of an embodiments of the disinfection system in conjunction with a surgical device having a channel, as well as a magnified view of a portion of the system according to the present disclosure.

DETAILED DESCRIPTION

Figure 1:
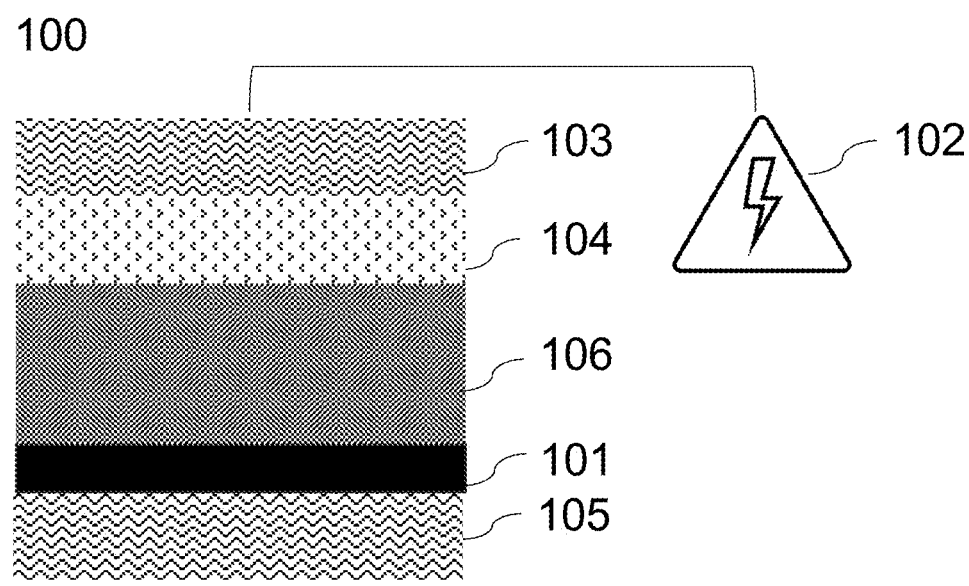
FIG. 1 is an illustration of direct and indirect plasma.
Figure 1:
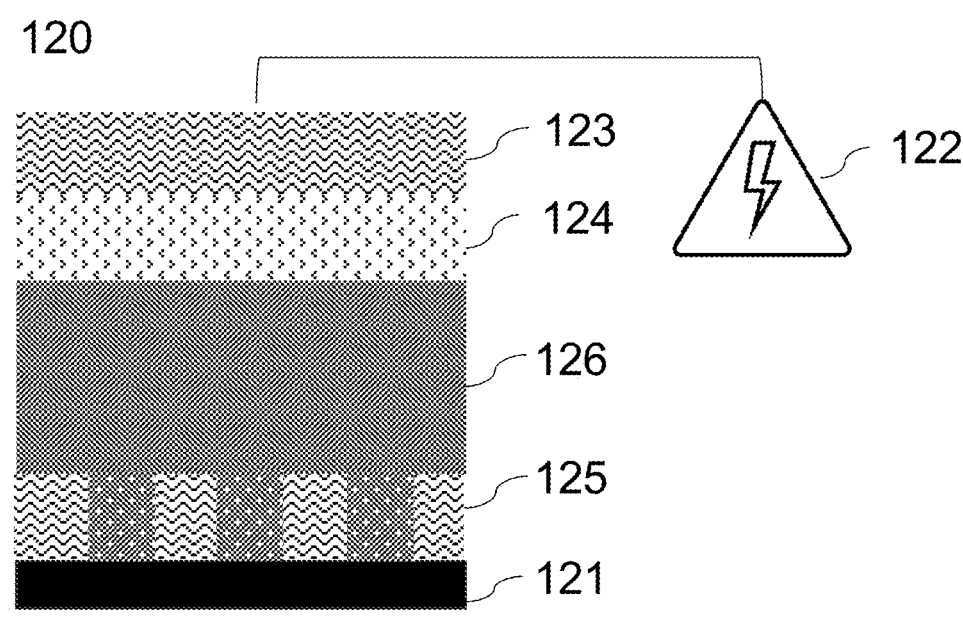

The description and the accompanying drawings are illustrative and should not be construed as limiting. Various mechanical, compositional, structural, and operational changes, including equivalents, may be made without deviating from the scope of this description and the claims. To avoid obscuring the disclosure, well-known structures and procedures have not been illustrated or detailed in depth in several cases. Items and their related aspects that are described in detail with reference to one embodiment may be included in other embodiments in which they are not specifically illustrated or described, whenever possible. For instance, if an element includes detail with reference to one embodiment but not with reference to another, the element may nevertheless be claimed to be included in the second embodiment. Furthermore, the depictions in this document are only illustrative and may not necessarily reflect the actual shape, size, or measurements of the system or portrayed components.

Duodenoscopes and other surgical devices have been known to house undesirable micro-organisms which are known to persist on the inner surface of channels such as working channels, as well as the elevator positioned at a distal end of endoscopes. These micro-organisms may form biofilms and include, for example, bacteria, prions, fungi, viruses, or other pathogens. Disinfecting working channels of these surgical device have become a challenge although, these microorganisms have been shown to be sensitive to application of plasma treatment. While the following disclosure is primarily directed to systems and method of disinfecting a channel of endoscopes such as a working channel, it should be understood that the features of the presently described disinfection system may be readily adapted for use with a variety of reusable or disposable instruments and devices and especially any surgical device having a channel. Working channels of endoscopes in particular tend to require disinfecting and are preferred embodiment of the present invention.

Disclosed herein are systems and methods for disinfecting channels of surgical devices from microbials present or suspected of being present on a channel (e.g., working channel) by use of plasma treatment produced under subatmospheric pressure. Specifically, systems and methods for disinfecting channels of surgical scoping devices are presented. The channel may be a working channel of an endoscope.

The term "surgical devices" may be used herein to mean any surgical device provided with a channel which is rigid or flexible. The channel is typically challenging to access for cleaning purposes. The surgical devices of the present invention may include robotic arms or surgical scopes introduced into a patient's body, such as a gastroscope, laparoscope, laparoscope, laryngoscope, sigmoidoscope, bronchoscopes, enteroscope, arthroscope, colonoscope, gastroscope, duodenoscope, endoscope, cystoscope, thoracoscope, cardioscope, etc., whether robotic or non-robotic, which include a working channel that is rigid or flexible.

As used herein, a channel is meant to include a tubular portion of a surgical device having a relatively narrow lumen which runs longitudinal within the surgical device. Although the term channel is used throughout this disclosure, it is possible to expand application of the present system to other hollow portions, cavities or crevices which are common in surgical devices. Surgical device channels are commonly used to deliver any one of a number of components including instruments (e.g., to a distally located robotic arms or surgical device), or biopsied tissue to and from a distal surgical site. These surgical device channels are sometimes referred to as working channels and may have a diameter of 5 mm or 4.5 mm or less. In a preferred embodiment a working channel of a surgical scope is targeted in plasma treatment.

The term "plasma" refers generally to a state of matter having an abundance of charged particles, e.g., electrons and ions. As used herein, the plasma of the current invention is low pressure direct plasma and is generated by applying an electric field which ionizes gas without significantly heating it. As known in the art, plasma may be generated, among other means, by dielectric barrier discharge, corona discharge, or glow discharge such as radiofrequency (RF) discharge. In radiofrequency (RF) discharge, a gas that may be in low pressure, such as subatmospheric ambient air, is ignited by a RF electrical discharge which generates an electromagnetic field. Ionization of the gas due to the electromagnetic field provides high energy particles which can modify the surface of substrate. The term "plasma cloud" is used to refer to the plasma formed from the ionized air.

The term "plasma generator" may include any system or combination of parts, such as a pair of spaced-apart electrodes, capable of generating plasma, that is, by igniting a gas (e.g., air) in a plasma zone by applying a strong electromagnetic field to the point where a gaseous substance is ionized and becomes increasingly conductive to transform into a plasma state referred to herein as a "plasma cloud". The term "generating plasma" is the act of igniting a gas by applying a strong electromagnetic field to the point where the gaseous substance is ionized and transforms into a plasma state referred to herein as a plasma cloud. The terms "energy transmission element" or "electrode" relates to an electrical contact made of a conductive material, such as metal, a semiconductor, graphite, conductive polymers, and any other material capable of conducting an electric current. An electrode may be an anode or a cathode, where electric current typically flows out of a cathode or discharge electrode and towards an anode or collecting electrode. In various embodiments of the present invention, igniting a gas is driven by the electrical potential difference between a pair of spaced-apart electrodes located on opposite sides of the working channel wall. The spaced-apart electrodes include the elongate discharge electrode and the conductive circumscribing sleeve (electrically associated with a collecting electrode).

"Power source" or "energy supply" are used interchangeably and refers to a source of radiofrequency or electromagnetic energy which is specifically located outside of the enclosure. The power source is adapted to supply electrical power having a frequency and/or a voltage in a defined range.

Referring to FIG. 1, subatmospheric direct plasma 100 of the present invention is illustrated and contrasted with indirect plasma 120. In both diagrams, channel surfaces 101 and 121 are the target for treatment. Power source 102 and 122 are configured to supply power to discharge electrodes 103 and 123 which each have an external dielectric material 104 and 124 between the electrode and the target object to be treated, in this case an inner surface of a channel. In each case, plasma 106 and 126 is formed, between discharge electrodes 103 and 123 and the object. In direct atmospheric plasma 100, the elongate discharge electrode forms part of the electric circuit in addition to the conductive circumscribing sleeve electrically coupled with the ground electrode 105. In indirect atmospheric plasma 120, the plasma generated between the discharge electrode 123 and ground electrode 125 is transported to the object through a passive diffusion and/or active convection mechanism, for example a plasma jet. Thus, in a first aspect, there is provided, a method of plasma-disinfecting an inner surface of a channel of a surgical device using direct plasma. The channel naturally contains ambient air, and the method is appropriate for a device having a conductive circumscribing sleeve surrounding the channel such as a standard endoscope. The method includes:

i. inserting the surgical device into a gas-sealable enclosure;

ii. positioning an elongate discharge electrode within the channel such that the elongate discharge electrode coaxially spans at least a lengthwise majority of the channel to define an annular ignition-region within the channel;

iii. electrically coupling (such as by contacting) a collecting electrode with the conductive circumscribing sleeve of the surgical device;

iv. gas-sealing the gas-sealable enclosure;

v. reducing a pressure of the annular ignition-region containing ambient air to a sub-atmospheric pressure; and vi. electrically igniting the ambient air of the annular ignition-region of the channel by applying an electrical potential difference to produce a longitudinal plasma cloud sufficient to disinfect the inner surface of the channel.

Plasma disinfecting refers to any reduction in contamination by microorganisms by the plasma generated. For example, a reduction in presence of living microorganisms on the inner surface of the working channel may be at least 3 log, at least 5 log or at least 8 log CFU per cm^2.

Although the method is adapted to disinfect the inner surface of a channel by direct application of plasma to the walls of the channel, other crevices or spaces connected to the channel may be exposed to a disinfecting plasma or a less direct plasma.

As used herein, ambient air refers to atmospheric air in its natural state and which naturally contains a mixture of gases, primarily nitrogen and oxygen, which can be ignited or ionized under low pressure conditions. Gases include any ionizable gas. Where the term ambient air is used, the device and methods may accommodate replacing the ambient air with an alternative ionizable gas or array of gases using a supply and means for delivery into the enclosure. The alternative ionizable gas may be a gas which is not naturally occurring in air or only partially present in air but provided to the channel. Examples of suitable inert gases include but are not limited to helium, argon, and nitrogen.

The method is specifically relevant for a device having a channel, as well as a conductive circumscribing sleeve which surrounds the channel coaxially. This is a typical component of a variety of scopes mentioned earlier.

As used herein, inserting the surgical device into a gas-sealable enclosure refers to placing the device inside the gas-sealable enclosure through an opening. As used herein, the term chamber and enclosure are used interchangeably and meant to define an enclosed space or volume for the low-pressure treatment to occur and are used interchangeably throughout. The gas-sealable enclosure or chamber refers to a container, canister, bag or any other containing means adapted to afford sealing off the inside volume from the outside environment. The gas-sealable enclosure includes a sealable opening in a wall which is sized to pass the channeled surgical device. After the surgical device is placed within the enclosure, the sealable opening is substantially gas sealable.

In some embodiments, the gas sealable enclosure is adapted for multi-use and is sterilizable. In other embodiments, the gas sealable enclosure is a sterile, single use product.

The walls of the enclosure may be rigid or flexible. In a preferred embodiment, the enclosure is a multilayer bag with an adapter embedded in its wall such that it forms a gas-sealed container.

As used herein gas-sealing may be hermetic and airtight, or it may be slightly permissive, as long as formation of plasma in the channel is possible.

In a preferred embodiment, the gas-sealable enclosure is suitable for storage upon completion of the plasma treatment. In this embodiment, the elongate electrode, as well as the collecting electrode may be removed from the enclosure while maintaining the disinfected state of the channel. In some cases, the pressure within the enclosure at the time of removal of the electrodes and/or storage is increased compared with the negative pressure state during ignition.

As used herein, the elongate discharge electrode refers to an electrode adapted to generate an electric field, when supplied with power, capable of ionizing the ambient air with subatmospheric pressure. The elongate discharge electrode has a longitudinal axis sized to coaxially span at least a lengthwise majority of the channel being treated. The elongate discharge electrode preferably has a circular transverse cross sectional shape relative to the elongate axis. For example, it may be a typical wire having an insulated dielectric outer layer adapted to form a uniform electric field. In some embodiments, it has an external diameter of from 0.5 to 1 mm+/−0.2. In some embodiments, it has length of at least 0.75 meter, at least 1 meter, or at least 1.5 meters.

The elongate discharge electrode has a conductive inner portion and an insulated and preferably dielectric outer layer. The conductive inner portion is made from an electrically conductive metal suitable for use as an electrode, for example, copper, stainless steel. gold, platinum, or the like. The surface layer may be a flexible ceramic material or a flexible polymer, such as a silicone elastomer. The elongate discharge electrode is adapted to set up an electric field in the annular ignition-region for igniting a plasma therein based on a connection to a power source located outside the enclosure which supplies RF and/or microwave energy. The connection to the power source may involve a coaxial cable.

Positioning an elongate discharge electrode within the channel refers to passing the elongate discharge electrode such that the electrode coaxially spans at least a lengthwise majority of the channel. As used herein, "coaxial" or "coaxially spanning" is meant to describe a position relative to the gas (e.g., ambient air) s of the channel. In some embodiments, the channel may be in a curved position while an electrode or specifically an elongate discharge electrode is coaxial relative to the working channel. Coaxially spanning at least, a lengthwise majority of the channel may refer to extending at least 60%, at least 70%, at least 80%, at least 90%, at least 100%, at least 105%, or at least 110% of the length of the channel. Positioning the elongate discharge electrode is most conveniently performed on an endoscope from the distal tip, where the scope lens is located and towards a proximal end of the channel, closer to the end with multiple ports on an endoscope for example. No additional conductive portion is present between the elongate discharge electrode and the inner surface of the channel.

Positioning an elongate discharge electrode within the channel defines an annular ignition-region within the channel. As used herein, "ignition region" refers to a location or volume within the channel where there is a simultaneous plasma ignition or a location or volume of space where gas (e.g., ambient air) contained therein is converted into a plasma. The ignition region has a cross-section of a ring or donut shape and can therefore be referred to as an annular ignition-region. The annular ignition-region typically spans a lengthwise majority of the channel, for example at least 0.75, 1 or 1.5 meter. The length of the central axis of the annular ignition-region is equivalent to the length of the channel, while the diameter of the outer perimeter is that of the channel (e.g., 1.2 to 4.2 mm) and the diameter of the central lumen is the diameter of the elongate discharge electrode. Typically, aside from ambient air or a replenished volume of air, no further components are contained in this space, and especially no conductive components which may interfere with application of plasma to the wall of the working channel.

Contacting a collecting electrode with a region of the conductive circumscribing sleeve of the surgical device refers to electrically connecting the collecting electrode, either directly or indirectly to an electrically connected region of the conductive circumscribing sleeve. A suitable electrically connected region of the conductive circumscribing sleeve may be the suction entry of an endoscope for example. The conductive circumscribing sleeve of a surgical scope can be a netted metallic tube which is typically present in an outer layer vis a vis the device channel. The collecting electrode is further electrically connected, by wire or touch mechanism, to a power source located outside of the enclosure.

Gas-sealable ports may include a seal dimensioned to sealingly circumscribe an external circumference of a conduit communicating between an inner volume of the enclosure and outside the enclosure.

Gas-sealing the gas-sealable enclosure refers to closing the opening or passage provided by the port for example, to pass the channel device while substantially isolating an inner pressure during treatment.

Once the channel device is in place, the opening in the enclosure may be closed such that it limits passage of air from and into the enclosure. The gas-sealing may be hermetic and airtight, or it may be slightly permissive, as long as formation of plasma in the channel is made be possible.

Sub-atmospheric pressure is any pressure which is less than that of the atmosphere. Typically, the negative pressure pump reduces the pressure within the chamber and therefore within the channel to sub-atmospheric. Due to the make-up and structure of the chamber, the pressure is subsequently maintained. It possible that the negative pressure pump will continue to reduce the pressure or alternatively, once the chamber reaches a target pressure, it may be maintained without continuous activity of the negative pressure pump.

Reducing a pressure of the annular ignition-region containing ambient air to a sub atmospheric pressure refers to reducing the pressure within the channel, typically by activation of a negative pressure pump, vacuum pump or a negative pressure source located outside of the enclosure. This may be by way of reducing the pressure in the enclosure which indirectly affects the pressure within the channel. Alternative and preferably and more directly, reducing the pressure of the ambient air present in the channel may be by fluidly connecting or associated with the lumen of the channel to a negative pressure pump, otherwise known as a vacuum pump. Reducing a pressure may involve physically connecting and gas-sealing the distal end of the channel and a gas-tight utility port in the wall of the enclosure. In this case, a gas-tight utility port is operatively connected to a negative pressure pump, the negative pressure pump operable to reduce the pressure in the channel.

Reducing the pressure may involve sealing any openings extending from the channel. Openings in the channel may be for example, a biopsy channel entrance or other access port. Sealing may involve applying a pressure resistant fitting to the ports to create a closed system, similar to those employed during the cleaning process for endoscopes. Reducing a pressure refers to suctioning access air and remaining fluid out of endoscope channel using suction or vacuum pump, also referred to as a negative pressure pump. This activity allows reaching a desired target negative pressure, such as less than 840 mBar (84 kPa) as well as maintaining the pressure for a desired duration. A pressure sensor may be employed to indicate that a target pressure has been reached. Reducing a pressure may involve an adapter with multiple ports, or a single port which may form part of the gas-sealable enclosure wall and operatively connects between the working channel on the inside of the enclosure, and a negative pressure pump on the outside of the enclosure, to remove gas prior to plasma ignition. The connection enables communication between an inner volume of the enclosure and a negative pressure pump or gas source. The connection on both sides of the enclosure is preferably gas-tight and the shape and size of the connection is therefore designed for optimum sealing. The port may further include an internal and single directional valve. The dedicated port for connecting the distal end of the channel or endoscope, may further include other openings to serve to pass elements requiring passage from inside to outside the enclosure.

In some embodiments, reducing a pressure of the annular ignition-region includes intermittently or periodically reducing a pressure. For example, the process may involve a reducing to pressure which is sub-atmospheric, pausing the negative pressure pump and then restarting the negative pressure pump to apply a negative pressure prior to a subsequent electrical ignition.

In some embodiments, reducing a pressure of the annular ignition-region comprises removing residue, being liquid, gas or a mixture thereof, prior to or after igniting the gas.

For example, removing residue may be from the enclosure and into a collecting canister. This step may be performed prior to or after igniting the gas in the channel for example during a periodic pause in ignition of the plasma cloud. In some examples, the residue may be removed via a filter. This residue may further be qualified to affect a decision on subsequent number or type of treatment steps. For example, repeating steps of the sterilization process may be recommended in certain cases.

Preferably, between the periodic application of negative pressure, a port for example, with a filter, is opened for entry of fresh ambient air. The intermittent reduction in pressure and provision of fresh ambient air enables application of a series of ignition cycles or production of multiple longitudinal plasma clouds to be applied to the surface of the channel. Alternatively, periodic application of negative pressure during the process may provide an opportunity to apply indirect plasma, that is, plasma generated in one location which has traveled, to reach areas which are difficult to reach and outside but continuous to or adjacent to the channel. In some cases, the pump is enabled to apply pressure to the channel on an opposing end from the initial treatment or alternatively connect to an opposing end (e.g., proximal end). In this process, the opposing end may be exposed to indirect plasma transferred from a first region to another, difficult to reach region with hard-to-reach crevices. These difficult to reach areas may include for example, the elevator region of an endoscope although other regions may also benefit.

In some embodiments, the method further includes reintroducing into the channel a fresh volume of air after electrically igniting the ambient air.

In some embodiments, reducing a pressure of the annular ignition-region includes expelling or removing gas or a plasma cloud exiting the channel towards a negative pressure pump via a filter. In further embodiments, reducing a pressure may include of removing gas, such as ionized gas out of the enclosure via a filter.

Electrically igniting the ambient air of the annular ignition-region of the working channel refers to applying an electrical potential difference between the elongate electrode and the conductive circumscribing sleeve to convert the subatmospheric ambient air into plasma. In some cases, the elongate discharge electrode is longitudinally static relative to the channel during disinfection.

The radiofrequency power supply (e.g., electromagnetic source) operably connected to the gas-sealable enclosure, by a wired or touch connection for example, can be controlled to electrically ignite (i.e., ionize) the ambient air of the annular ignition-region of the working channel by applying an electrical potential difference, such as a radiofrequency voltage, or driving a radial electric field between the elongate electrode and the conductive circumscribing electrode structures. The voltage is sufficient to ignite a plasma in the electrically non-conductive ambient air under low pressure within the lumen and further sufficient in terms of voltage and in terms of the period of time to apply a direct plasma to the wall to disinfect the inner surface of the working channel. Applying an electrical potential difference results in a radial plasma cloud which has the shape of a thick-walled tube and extends towards and preferably contacts or comes in close proximity to the inner surface of the channel. The perimeter of the radial plasma cloud is proximate to the inner surface of the channel and may contact or even extend beyond an inner surface of the channel. In some embodiments, the radial plasma cloud spans at least a lengthwise majority of a distal half of a working channel, where the distal end includes the optic lens. The longitudinal plasma cloud may be sufficient to disinfect the inner surface of a working channel.

In some embodiments, applying an electrical potential difference between the elongate discharge electrode and the conductive circumscribing sleeve is along a coaxial length of a channel of at least 0.75, 1 or 1.5 meter. In some embodiments, a voltage sufficient to disinfect is from about 3 kV to about 10 kV. In some embodiments, a suitable time period sufficient to disinfect is less than 12 minutes, less than 10 minutes, less than 8 minutes or less than 6 minutes or between 5 and 10 minutes. In some embodiments, a surgical device exterior and/or a distal most end, such as a distal most end (e.g., such as an endoscope elevator) relative to the connection to the pressure pump is further exposed to indirect plasma. Distal most end in this context and as applied to an endoscope is a distal end relative to the negative pressure pump connection or the surgeon proximate end. Indirect plasma refers to ionized molecules from the plasma region which have traveled to a second region. Indirect plasma in this context is meant to relate to plasma which was generated in one location and transported and therefore has lost some of its effect on the surrounding. Nonetheless, it may fill a role in hard-to-reach locations. The exterior, contained within the enclosure, may also be exposed to indirect plasma due to less than hermetic sealing of the channel.

In a particularly preferred embodiments, upon completion of treatment, the surgical device is stored in the enclosure until use. In that case, connections are disassociated from the external ports of the enclosure or adapter, and gas sealable ports having single directional valves.

Embodiments of the present invention will now be described in more detail by way of example only with reference to the accompanying drawings. Some of the drawings, are not to scale and some dimensions may be exaggerated for the purpose of clarity of illustration.

Figure 2:
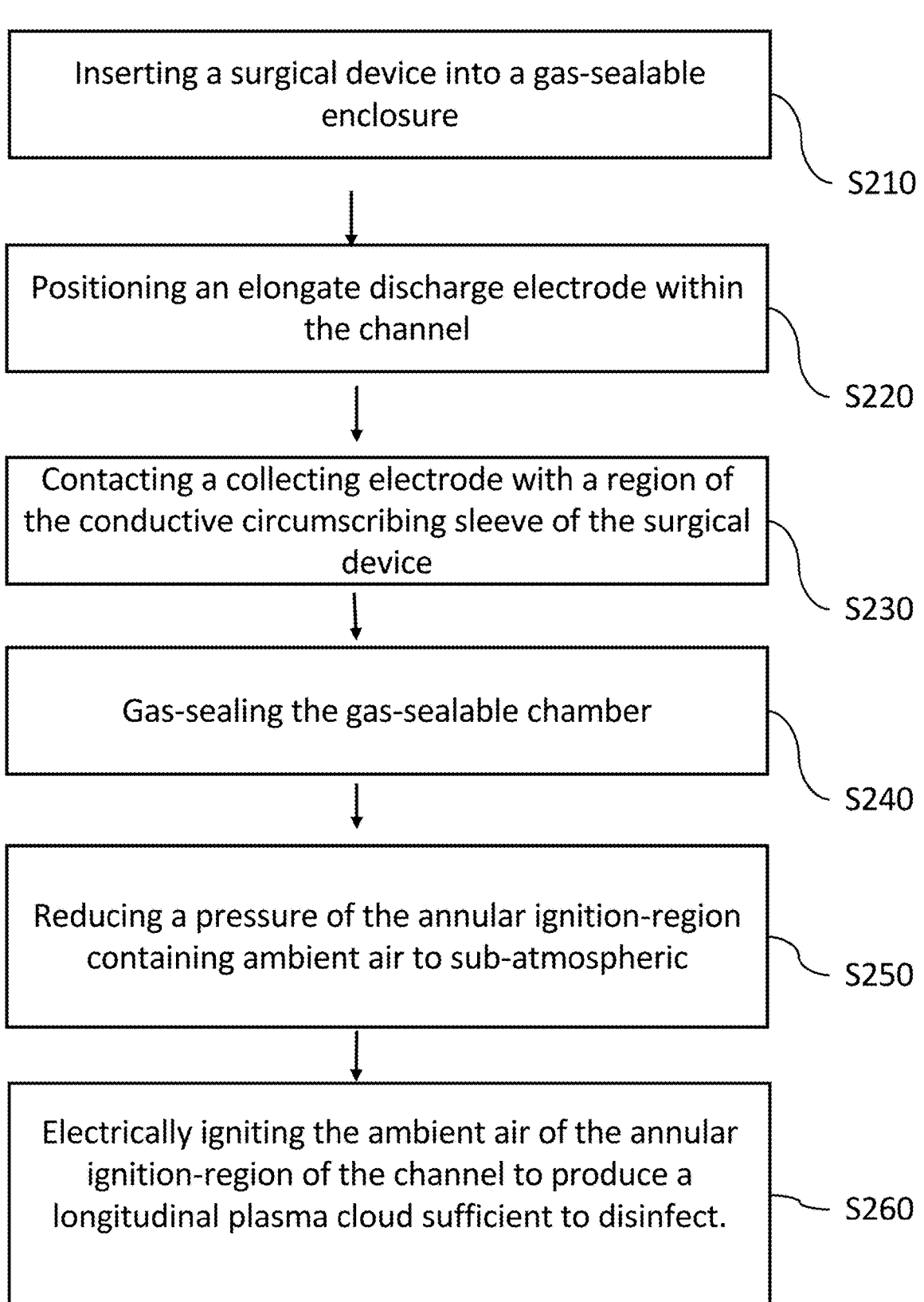
FIG. 2 is a flow chart version of the method for disinfection according to the present invention.

Referring to FIG. 2, in one aspect, there is provided, a method of disinfecting an inner surface of a channel of a surgical device, said channel containing gas (e.g., ambient air) and having a conductive circumscribing sleeve surrounding the channel. At step S210, the method includes a step of inserting the surgical device into a gas-sealable enclosure or chamber, herein also referred to as a "chamber" or "enclosure". The method includes, positioning an elongate discharge electrode within the channel in step S220. In this step, the elongate discharge electrode is positioned such that it coaxially spans at least a lengthwise majority of the working channel to define an annular ignition-region within the channel. The method further includes contacting a collecting electrode with a region of the conductive circumscribing sleeve of the surgical device or an electrically connected region of the circumscribing sleeve in step S230. The method further includes gas-sealing the gas-sealable enclosure or the annular ignition-region comprising gas (e.g., ambient air), in step S240. The method further includes reducing the pressure of the annular ignition-region containing a gas to sub-atmospheric in step S250. For example, this may be by reducing the pressure of the gas-sealable chamber. The method may further include electrically igniting the gas (or ambient air) of the annular ignition-region of the channel by applying an electrical potential difference between the elongated discharge electrode and the conductive circumscribing sleeve sufficient to produce a longitudinal plasma cloud sufficient to disinfect in step S260.

Positioning an elongate discharge electrode within a channel in step S220, may be such that the elongate discharge electrode coaxially spans at least a lengthwise majority of the channel to define an annular ignition-region within the channel. In some embodiments, positioning may involve using a motorized positioning apparatus configured to advance the elongate discharge electrode through a length of the channel such that it coaxially spans at least a lengthwise majority of the channel.

In step S230, contacting a collecting electrode with a region of the conductive circumscribing sleeve of the surgical device.

In step S240, gas-sealing the annular region comprising gas. In some embodiments, gas-sealing may be limited to the annular ignition-region. In some embodiments, gas-sealing the annular ignition-region and reducing a pressure therein to sub-atmospheric may occur within a chamber in which the surgical device is placed. In some embodiments, the gas-sealing the annular ignition-region and reducing the pressure therein to sub-atmospheric may be provided by sealing a gas-sealable door (herein referred to as a "door") of a chamber, further having a gas-tight utility port in fluid communication with a negative pressure source.

In step S250, reducing a pressure of the annular ignition-region containing a gas to sub-atmospheric. In some embodiments, the reducing a pressure therein to sub-atmospheric is to a pressure of less than 500 mbar. In some embodiments, the reducing a pressure therein to sub-atmospheric is to a pressure of less than 200 mbar. In some embodiments, the reducing a pressure therein to sub-atmospheric is to a pressure of less than 100 mbar. In some embodiments, the reducing a pressure therein to sub-atmospheric is to a pressure of less than 50 mbar. In some embodiments, the reducing a pressure therein to sub-atmospheric is to a pressure of less than 20 mbar. In some embodiments, reducing a pressure of the annular ignition-region containing gas (e.g., ambient air) to sub-atmospheric involves activation of a negative pressure pump outside of the gas-sealable chamber.

In step S260, electrically igniting the gas (e.g., ambient air) of the annular ignition-region of the channel by applying an electrical potential difference between the elongate discharge electrode and the conductive circumscribing sleeve to produce a longitudinal plasma cloud sufficient to disinfect the inner surface of the channel. In this way, the method employs the use of gas (e.g., ambient air). By producing an electric field, the elongate discharge electrode is able to generate and sustain a plasma from the air for sterilization of the channel of the scoping device.

In another aspect of the present invention, there is provided, a disinfection system for plasma-disinfecting an interior surface of a channel of a surgical device having a conductive circumscribing sleeve surrounding the channel, said disinfection system comprising: i. a pair of spaced-apart electrodes located on opposite sides of a channel wall, said electrodes configured to apply an ionizing electric field radially and over a lengthwise majority of the elongate discharge electrode; ii. a gas-sealable enclosure having a gas-sealable opening (e.g., door) sized to receive a surgical device and one or more gas-tight utility ports spanning a wall of the gas-sealable enclosure, said gas-tight utility ports adapted to (a) fluidly connect between a negative pressure source on the outside and an end of a channel on the inside; and (b) electrically couple between a power source on the outside and the pair of spaced-apart electrodes on the inside; and iii. a controller said controller configured, when a combination of (a) the gas-sealable enclosure, (b) the pair of spaced-apart electrodes, and (c) the channel are in a ready-to-ignite-plasma state, to electrically ignite at least some ambient air to form plasma, so as to disinfect an inner surface of the channel.

In some embodiments, the pair of spaced-apart electrodes located on opposite sides of the channel wall comprise: an elongate discharge electrode optionally having a dielectric exterior or outer surface, and a collecting electrode adapted to electrically couple with a conductive circumscribing portion of the surgical device.

In some embodiments, a ready-to-ignite state requires all of the following: at least a section of the elongate discharge electrode is disposed within the channel of the surgical device so that the elongate discharge electrode coaxially spans at least a lengthwise majority of the channel to define an annular region within the channel; the collecting electrode is electrically coupled to the conductive circumscribing sleeve of the surgical device; the gas-sealable enclosure is gas-sealed and a negative pressure pump is activated such that said annular region is maintained at a sub-atmospheric pressure.

In some embodiments, the controller is configured to control the voltage, current and frequency of an electrical power source. In some embodiments, the controller is further configured to control intermittent application of a negative pressure to the channel or enclosure. In some embodiments, the controller is further configured to control intermittent application of a negative pressure to opposing ends of the channel.

In some embodiments, the one or more gas-tight utility ports spanning a wall of the enclosure are organized on a single adapter.

In some embodiments, a collection chamber is further associated with the enclosure. The collection chamber is configured to receive liquid residue upon application of negative pressure prior or after to ignition of plasma. Liquid residue is commonly present at the end of a standard cleaning process for endoscopes. The collection chamber may also be associated with the negative pressure pump.

In some embodiments, the elongate discharge electrode has a length of more than 0.75, 1 or 1.5 meter. In some embodiments, the elongate discharge electrode is configured to drive a radial electric field towards a circumscribing conductive circumscribing sleeve of the surgical device. In some embodiments, the elongate discharge electrode further includes a motor configured for advancing the elongate discharge electrode through a length of the channel.

In some embodiments, the collecting electrode adapted to attach to a port of an endoscope which is electrically associated with a conductive circumscribing sleeve. In some embodiments, the controller is configured to activate the power source and for a time period sufficient to cause a reduction of contamination on an inner channel surface. In some embodiments, the enclosure further includes an air inlet for enabling passive entry of air.

In some embodiments, the enclosure further includes a pressure relief valve extending through the wall of the enclosure configured to allow air or gas to flow in or out of the enclosure. In some embodiments, the enclosure further comprises one or more plasma exhaust ports extending through said walls of the enclosure and configured to release plasma exhaust or waste. In some embodiments, the exhaust port further comprises a filter configured to filter ozone or other by products of the disinfection treatment. In some embodiments, the enclosure is configured for multiple use. In some embodiments, the enclosure is configured for single use. In some embodiments, the enclosure is flexible but includes structural support to maintain an inner volume surrounding the surgical device despite sub-atmospheric pressure applied.

In some embodiments, the system further comprises at least one of (i) inserting-means for bringing an elongated discharge electrode into an insert-state relative to the channel so that the elongate discharge electrode coaxially spans at least a lengthwise majority of the channel to define an annular region within the channel; and (ii) detecting means for detecting if the elongated discharge electrode is in said insert-state relative to the channel.

Figure 3:
FIG. 3 is a surface view illustration of the system according to the present invention.

Referring to FIG. 3, a plasma-disinfecting system 310 according to an aspect of the invention is schematically portrayed. The plasma-disinfecting system 310 is adapted to reduce contamination of microorganisms on an inner surface of a working channel of a surgical device. The plasma-disinfecting system includes a gas-sealable enclosure 312, herein "enclosure", a plasma generator and a controller 350. The gas-sealable enclosure 312 includes a gas-sealable opening 340 sized to receive a surgical device and one or more gas-tight utility ports 360 spanning a wall of the gas-sealable enclosure. A gas-tight utility ports fluidly connect between a negative pressure source 330 on the outside and an end of a channel on the inside. In addition, an additional gas-tight utility port electrically couples between a power source 320 on the outside and the pair of spaced-apart electrodes on the inside, by way of utility line 322 which supplies power to the elongate discharge electrode and utility line 324, which connects with the collecting electrode, otherwise known as a ground electrode. In this embodiment, the one or more gas-tight utility ports spanning a wall of the enclosure are organized on a single adapter 361. Controller 350 is configured, when a combination of (a) the gas-sealable enclosure, (b) the pair of spaced-apart electrodes, and (c) the channel are in a ready-to-ignite-plasma state, to electrically ignite at least some ambient air to form plasma, so as to disinfect an inner surface of the channel.

Figures 4A, 4B:
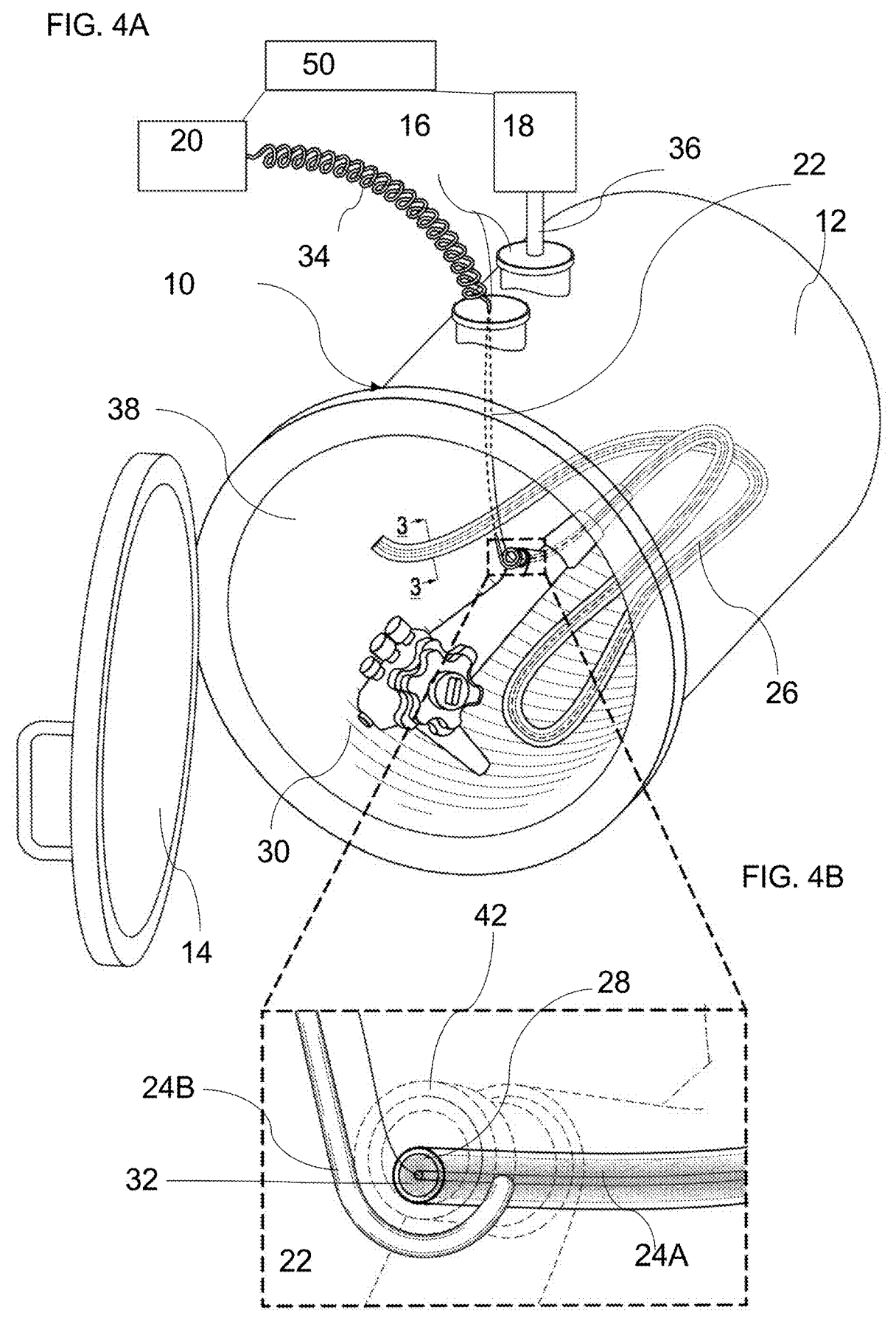
Figure 5:
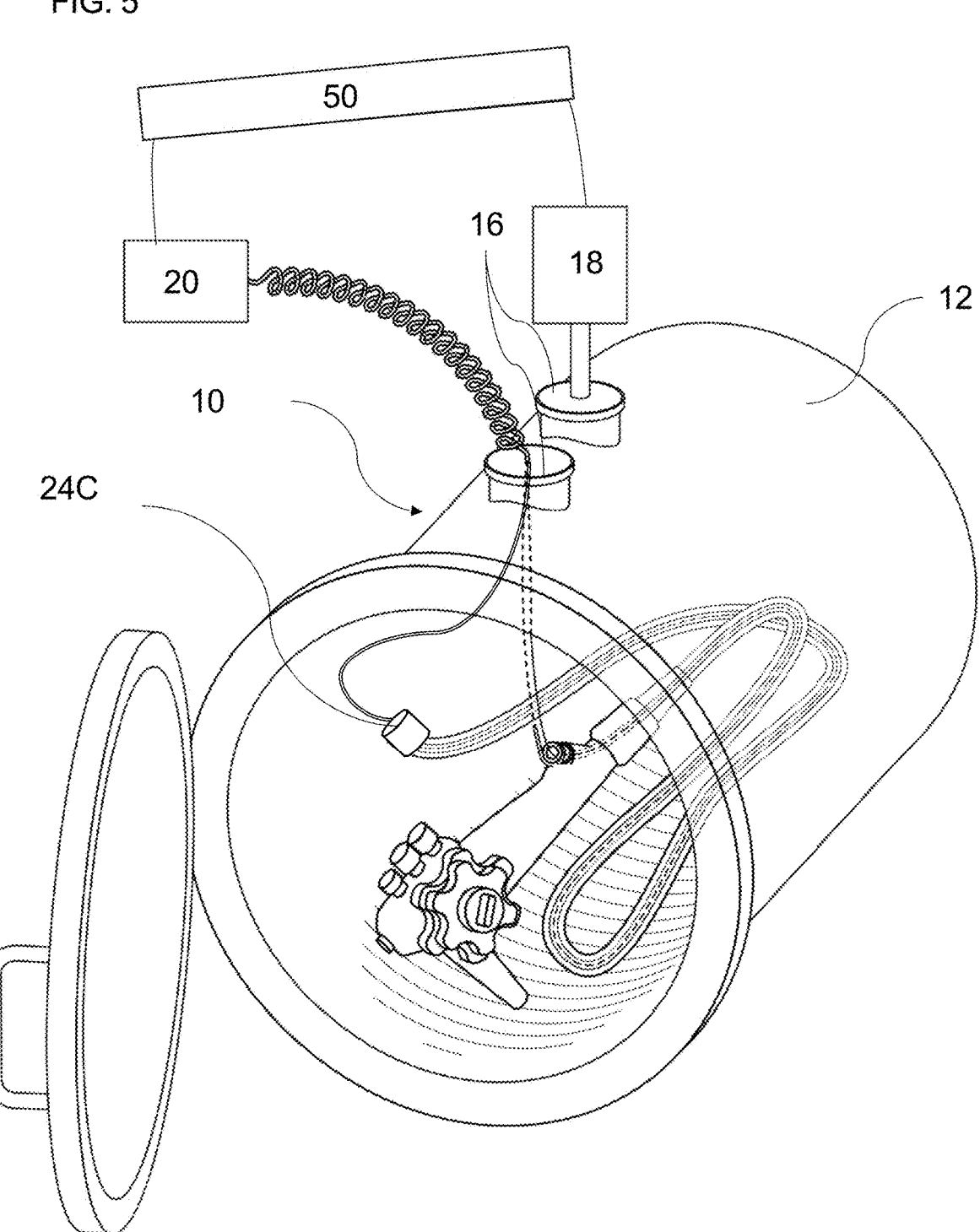
FIG. 5 illustrates an orthogonal view of an additional embodiment of the disinfection system having an additional electrode, a cap-shaped discharge electrode configured to cap a distal tip of the surgical device.

Referring to FIG. 4A, FIG. 4B, and FIG. 5, a plasma-disinfecting system 10 according to an aspect of the invention is schematically portrayed. The plasma-disinfecting system 10 is adapted to reduce contamination of microorganisms on an inner surface 32 of a working channel 26 of a surgical device 30. The surgical device typically includes a conductive circumscribing sleeve 42 surrounding the working channel 26. A conductive circumscribing layer of a surgical scope can be a netted metallic tube which is typically present in an outer layer vis a vis the working channel. The plasma-disinfecting system includes a gas-sealable chamber 12, herein "chamber", a plasma generator 22 and a controller 50.

The plasma generator 22 comprises an elongate discharge electrode 24A, and a collecting electrode 24B, each electrically associated with a power source 20, said plasma generator configured to apply an ionizing electric field radially from the elongate discharge electrode 24A and over a lengthwise majority of the elongate discharge electrode 24A. Note there is no relative longitudinal motion of the electrode within the channel during the plasma generation process but rather the elongate electrode is stationary throughout. In some embodiments, the elongate discharge electrode 24A is further configured for placement in a relatively central cross-sectional or axial position of the working channel 26. In some embodiments, the elongate discharge electrode 24A drives a radial plasma cloud 28 or plasma cloud towards the working channel inner surface 32 or walls of the working channel 26. In some embodiments, a spacer surrounds the elongate discharge electrode 24A such that a distance exists between the electrode and the channel wall or such that there is minimal contact with the channel wall. However, in some embodiments, the wire contacts an inner wall while providing sufficient plasma treatment to an opposing inner wall surface. The elongate discharge electrode 24A may have a wire-shape and may be formed of conductive material. In some embodiments, the elongate discharge electrode 24A is configured for dielectric isolation. In some embodiments, the elongate discharge electrode 24A is constructed of a double wire. In some embodiments, the elongate discharge electrode 24A is configured with a blunt end or electrically isolated distal end to prevent effect on the channel walls during deployment and ensure electrical safety during use. In some embodiments, the elongate discharge electrode 24A is further configured to promote drying of the walls of the working channel 26 as it is positioned for example by including an absorptive material or a fanning element. For example, an absorbing cloth may surround the distal end and absorb any liquid on the surface of the channel wall. In some embodiments, the elongate discharge electrode 24A and the channel wall define an annular ignition-region containing ionizable gas or ambient air.

The elongate discharge electrode 24A is sized and shaped for longitudinal placement within a working channel and the collecting electrode is adapted to electrically associate with a conductive circumscribing portion of the surgical device. The elongate discharge electrode 24A has a length of more than 1.5 meters. Elongate discharge electrode 24A may further includes a motor configured for advancing the elongate discharge electrode through a length of the working channel.

Gas-sealable enclosure 12, may be rigid as in a chamber or flexible as in the case of a bag. Gas-sealable enclosure 12 is associated with a negative pressure pump 18. The chamber 12 has a gas-sealable door and one or more gas-tight utility ports. The controller 50 is configured, when a combination of the chamber 12, the plasma generator 22, and the working channel 26 is in a ready-to-ignite-plasma state, to electrically ignite at least some gas (e.g., ambient air) to form plasma, so as to disinfect an inner surface of the surgical device.

In some embodiments, the power source 20 is an electromagnetic source including but not limited to a radio frequency electromagnetic energy or microwave electromagnetic energy. The energy source is coupled to the energy transmission element and configured to transmit sufficient energy (e.g., in the form of an electric field) radially outward along the length of the working channel 26 to at least sanitize, and preferably to disinfect, at least a portion of the working channel 26 of the endoscopic instrument. In this context, "microwave frequency" may be used broadly to indicate a frequency range of between 300 MHz to 300 GHz, but preferably the range 1 GHz to 300 GHZ. "Radiofrequency" or "RF" may be used broadly to indicate a frequency range of up to 300 MHZ, preferably 1 kHz to 100 MHz. In some embodiments, the power supply may comprise an alternating current (AC) direct current (DC), or other suitable power supply configured to create electric arc discharges, corona discharges and/or dielectric barrier discharges within the working channel 26.

Elongate discharge electrode 24A is positioned within the center of working channel 26 in a preferably contactless manner such that it coaxially spans at least a lengthwise majority of channel 26 to define an annular region therein. In one embodiment, the proximal-distal end axis of the elongate discharge electrode 24A is co-directional with proximal-distal end of the channel 26. In another embodiment, the proximal-distal end axis of the elongate discharge electrode 24A is aligned with but opposite to the proximal-distal end of the channel 26.

The collecting electrode 24B is in contact with a region of conductive circumscribing sleeve 42 of surgical device 30 and configured to close an electrical circuit and specifically to receive from elongate discharge electrode 24A. Chamber 26 is subsequently gas-sealed by closing gas-sealable opening 14 and negative pressure pump 18 is activated such that the chamber and therefore the annular region is maintained at a sub-atmospheric pressure. A ready-to-ignite state requires all of the following: elongate discharge electrode in channel, collecting electrode 24B in contact with a region of conductive circumscribing sleeve 42, and gas-sealing and reducing the pressure to sub-atmospheric. The plasma generator is subsequently activated, whether by user or alternatively controlled by controller 50, which drives a radial electric field towards a conductive circumscribing sleeve of the surgical device. The collecting electrode 24B may include a hook shape configured to fit or fixate the collecting electrode 24B to the conductive circumscribing portion of the surgical scope. In some embodiments, the collecting electrode 24B may be positioned on an inner wall of the chamber 12 and be configured or shaped to function as a hook to receive, position, attach or hold the surgical device 30 in place. In other embodiments as portrayed in FIG. 3, collecting electrode 24B is configured to contact the conductive circumscribing sleeve 42 of the surgical device 30 at a single point.

Controller 50 may be configured, to electrically ignite at least some gas (e.g., ambient air) to form plasma, contingent upon a combination of all of: chamber 12, the plasma generator 22, and channel 26, being in the ready-to-ignite state. Controller 50 may be configured detect that a combination of the chamber 12, the plasma generator 22, and the channel 26 are in the ready-to-ignite state prior to electrically igniting at least some gas (e.g., ambient air) to form plasma. In some embodiments, the controller may be configured to activate the power source 20 for a time period sufficient to cause the inner channel surface 44 to undergo a reduction of contamination. In some embodiments, the controller may be configured to activate or regulate the power source 20 at a voltage sufficient to cause the inner channel surface 44 to undergo a reduction of contamination. In some embodiments, the controller may be configured to activate or regulate the negative pressure source at a pressure to cause the inner channel surface 44 to undergo a reduction of contamination. In some embodiments, the controller may be configured to periodically introduce a source of ionizing gas into the chamber 12 to cause the inner channel surface 44 to undergo a reduction of contamination. In some embodiments, the controller may be configured to periodically remove ionized gas from the chamber 12.

The controller 50 may be configured to be automatic or to be operated by a medical practitioner, possibly including user interface components such as switches, navigating sticks, touch screens, and touch pads. The controller 50 may be associated with a memory. The controller 50 may include a processor configured to control electricity flow through the electrodes to cause an ionizing electric field associated with a voltage drop between the first electrode and a collecting electrode to thereby generate plasma within the plasma-activation region; and maintain the generated plasma in the ignition-region for time period sufficient to cause the surface to become disinfected. At least one processor may be commutatively coupled to at least one memory using wired and/or wireless means. At least one processor may be further electrically coupled to power supply and circuity. At least one processor may be configured to execute one or more program code instructions with respect to one or more data items stored in at least one memory. The at least one program code instruction may facilitate control of one or operational aspects of the plasma generator system, e.g., to control the generation of plasma. For example, at least one processor may control and moderate one or more attributes of energy supplied by the power supply to plasma applicator for the purpose of generating plasma to treat an object, for example by controlling one or more components of circuity.

Figure 6:
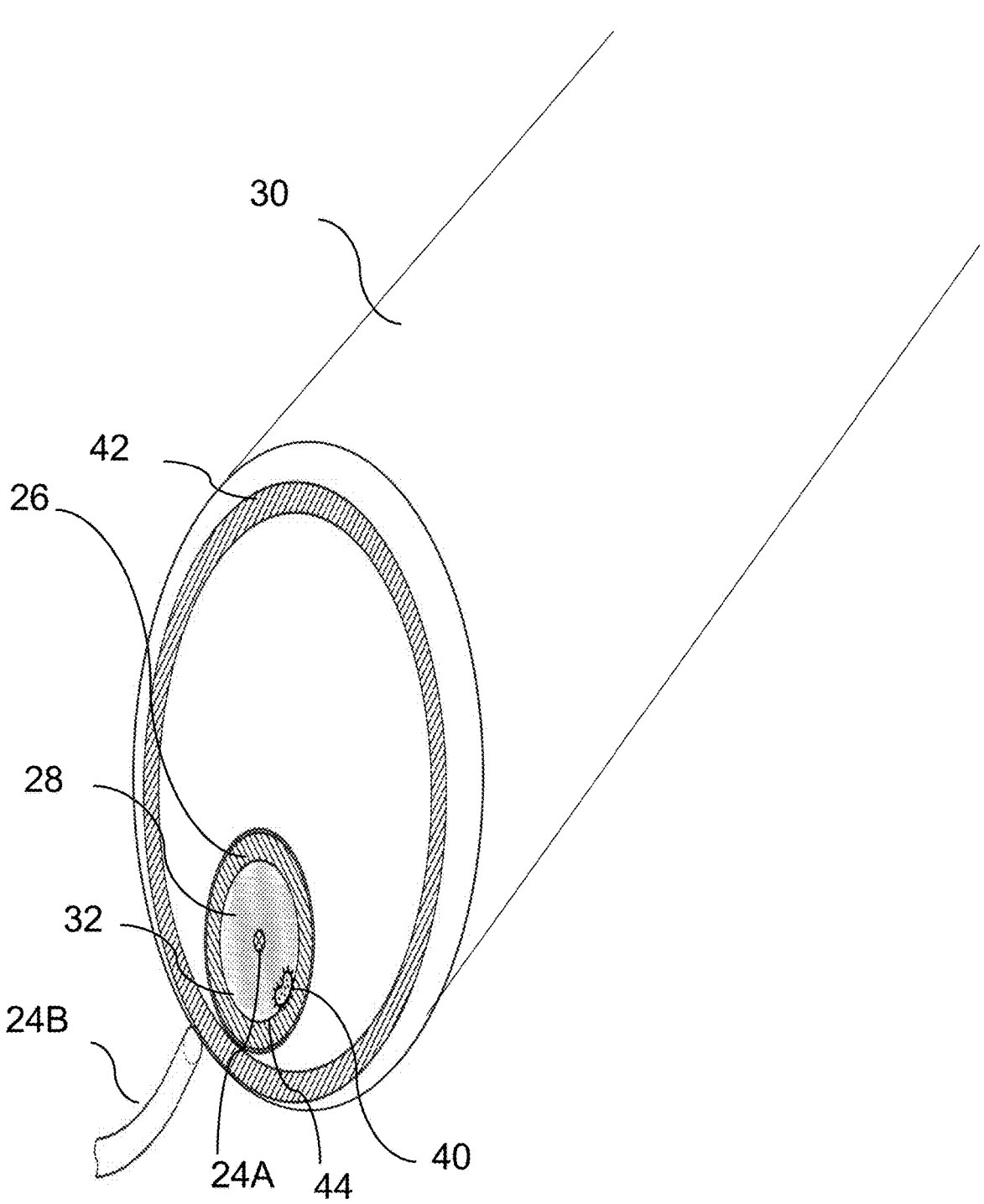
FIG. 6 illustrates a lateral cross-sectional view of the distal end of surgical device having a channel with positioning of the two electrodes of the disinfection system.

In FIG. 6, schematically shows an orthogonal view of the distal end of working channel 26 of a surgical device 30 when the plasma generator 22 is active and plasma is formed such that the surface of the channel is treated. In some embodiments, the plasma cloud formed is preferably uniform. A period of time with plasma cloud 28 is sufficient to affect the viability of microorganism 40 on an inner channel surface 44 of the working channel.

In some embodiments, the electrically igniting the gas of the annular ignition-region spans at least a lengthwise majority of a proximal half of the channel 26 or a proximal half of the elongate discharge electrode 24A. In some embodiments, applying an electrical potential difference does not require maintaining the potential difference at a given constant value. In some embodiments, electrically igniting the gas is without relative longitudinal motion between wire and the channel. In some embodiments, the ignition-region of the elongate discharge electrode 24A includes both (i) location(s) in the distal most 25% of the region of the elongate discharge electrode 24A that is co-axial to and disposed within the channel; and (ii) location(s) in the proximal most 25% of the region of the elongate discharge electrode 24A that is co-axial to and disposed within the channel. In some embodiments, electrically igniting the gas of the annular ignition-region of the channel 26 to produce a longitudinal plasma cloud sufficient to reduce the presence of living microorganisms on the inner surface of the channel 26 by at least 3 log CFU per cm^2. In some embodiments, the plasma is sufficient to reduce the presence of living microorganisms is by at least 5 log reduction in CFU per cm^2. In some embodiments, is the plasma is sufficient to reduce the presence of living microorganisms is by at least 8 log reduction in CFU per cm^2. In some embodiments, electrically igniting the gas is for a sufficient period of time to reduce a presence of living microorganisms.

In some embodiments, the igniting the gas is by applying an electrical potential difference between the elongate discharge electrode 24A which coaxially spans at least a lengthwise majority of a portion of the channel 26. Although an electrical potential difference is applied, there is no requirement for maintaining a potential difference at a given constant value. In some embodiments, the igniting the gas is by applying an electrical potential difference between the elongate discharge electrode 24A and collecting electrodes is for a period of time sufficient to disinfect the inner surface of the channel 26. In some embodiments, the igniting the gas is by applying an electrical potential difference between the elongate discharge electrode 24A which coaxially spans in a manner which is preferably substantially contactless. In some embodiments, igniting the gas is by applying an electrical potential difference between the elongate discharge electrode 24A and the conductive circumscribing sleeve, said elongate discharge electrode 24A being longitudinally static relative to the channel 26 for a period of time to disinfect.

In some embodiments, elongate discharge electrode 24A may have a length of more than 0.5, 1.5 or 2 meters. The elongate discharge electrode 24A may have a diameter of 2.5, 1.5, 0.7 mm or less which may be suitable for particularly narrow channels. The maximum diameter of the portion of the elongate discharge electrode 24A which spans the working channel 26 should ensure sufficient volume for the presence of ionizable gas to sustain a plasma within the working channel 26. Said another way, there should be sufficient volume of air between the elongate discharge electrode 24A and the inner walls of the working channel 26.

In some embodiments, igniting the gas is by applying an electrical potential difference between the elongate discharge electrode 24A and the conductive circumscribing sleeve is along a coaxial length of a channel 26 of at least 0.75, 1, 1.5 or 1.8 meter. In some embodiments, the igniting the gas is by applying an electrical potential difference between the elongate discharge electrode 24A and the conductive circumscribing sleeve, said elongate discharge electrode 24A having a lengthwise majority being a conducting outer-surface which is uninsulated.

In some embodiments, the method further comprises a stage of drying the inner surface of the channel 26 prior to electrically igniting the gas.

In some embodiments, the surgical device further includes a distal end having crevices such as an elevator region. In this case, the method may further include applying to a surgical device tip an additional discharge electrode being a cap-shaped discharge electrode 24C, configured to form a cap over the elevator region and electrically igniting a gas to form plasma in an area of the elevator. In some embodiments, the elongate discharge electrode 24A and the cap-shaped discharge electrode 24C are a multiple use electrode. In some embodiments, the elongate discharge electrode 24A is a single use or disposable electrode, and the cap-shaped discharge electrode 24C is a multiple use electrode. In some embodiments, the elongate discharge electrode 24A and the cap-shaped discharge electrode 24C are each a single use or disposable electrode. In some embodiments, the multiple use is sterilizable. In this case too, the collecting electrode 24B, at a proximal end, is electrically connected to a conductive circumscribing sleeve 42 which forms a part of the surgical device 30 along the channel 26. Thus, the cap-shaped discharge electrode 24C produces a plasma cloud extending towards the conductive tip which is electrically associated with the conductive circumscribing sleeve 42 and eventually to the collecting electrode 24B to generate plasma in the elevator region. The cap-shaped discharge electrode 24C may also include a faucet structure coupled to a gas supply to provide gas to the working channel 26 region periodically.

In some embodiments, a chamber 12 is configured to isolate an inner volume of the chamber housing from the surrounding atmosphere. The chamber 12 includes a gas-sealable opening or door 14 and one or more gas-tight utility ports 16. The gas-sealable opening 14 is sized to enable insertion and extraction of the surgical device. Although a passage for the surgical device is provided, the opening 14 is gas-sealable such that substantially no gas is exchanged from the inner volume of the chamber 12 and outside the chamber 12. As used herein, an opening 14 is a closure device, optimally a gas-tight closure device, which may be opened and closed in a reversible manner and be configured to seal an entrance. In some embodiments, chamber 12 in its closed state may contain a gas (e.g., ambient air) having an opening with a collar, to which door is secured. The gas-sealable opening 14, when closed, may form at least a portion of a gas (e.g., ambient air) of the gas-sealable chamber 12. Similar to the gas-tight utility port 16 described herein, the gas-sealable opening 14 may contribute to ensuring that a user has full control over the amount of ionizable gas which is present in the gas-sealable chamber 12.

In some embodiments, the chamber 12 is sized and shaped to house a surgical device or part thereof. In some embodiments, the chamber 12 is sized and shaped to house a plurality of surgical devices or parts thereof. Any shape may be used whether symmetrical or shaped to accommodate a specific contour of a surgical device. For example, it is possible that chamber 12 is wide at the top to accommodate the user interface end with valves and knobs while being long and narrow at the bottom to accommodate the bendable distal end. The gas-sealable chamber 12 may include a chamber body having multiple chamber gas (e.g., ambient air) s or a tubular chamber gas (e.g., ambient air) which defines an outside from a chamber interior region 38.

In some embodiments, the chamber 12 is configured for single use. In some embodiments, the chamber 12 may have flexible walls. In some embodiments, the chamber 12 may be a disposable chamber such that it is prepared from a disposable material such as a plastic or even nylon. The chamber 12 is closed and sealed by a "zip lock" mechanism. While the disposable chamber may be inexpensive and preferred for single sterile use, in some embodiments, the disposable chamber further includes structural support in the walls of the chamber 12 to promote maintenance of an inner volume within the chamber under negative pressure conditions. One of the advantages of the disposable chamber is that the processed scope may subsequently be stored until use within a sterile disposable chamber. In some embodiments, door 14 is a made up of a joint system having an opposed first and second surfaces configured to enable engagement with each other in response to a force applied for example by a zip lock system. The chamber 12 may be portable or designed for stationary deployment.

In some embodiments, the gas-sealable chamber 12 is configured for multiuse use. The shape and material which make up the gas-sealable chamber 12 are therefore selected based on the ability to provide an inner volume having a substantially isolated pressure. In some embodiments, the multiuse chamber is configured to be sterilized after use. In some embodiments, the chamber 12 is shaped to support a multiple use vacuum chamber for example being cylindrical which may provide increased strength to withstand multiply applications of negative pressure. The chamber 12 may be made from material which is suitable for sterilization and multiply applications of negative pressure. For example, it may be made from aluminum. In some embodiments, a window may be included in a chamber wall for observation and monitoring the process. The bottom of the chamber 12 may include a drain port configured to drain access fluid. The chamber 12 is configured to maintain a pressure communicated and defined by the negative pressure source. Said another way, it is constructed from materials, shaped, and designed generally to be pressure isolated. In some embodiments, the chamber 12 is configured to maintain a pressure for a period of time to generate sufficient plasma to affect the surrounding gas (e.g., ambient air) s of the channel 26. In some embodiments, the chamber 12 is configured to maintain a pressure of less than 300 mbar for a period of time to generate sufficient plasma to affect the surrounding gas (e.g., ambient air) s of the channel 26. In some embodiments, the chamber 12 is configured to maintain a pressure of less than 200 mbar for a period of time to generate sufficient plasma to affect the surrounding gas (e.g., ambient air) s of the channel 26. In some embodiments, the chamber 12 is configured to maintain a pressure of less than 100 mbar for a period of time to generate sufficient plasma to affect the surrounding gas (e.g., ambient air) s of the channel 26. In some embodiments, the chamber 12 is configured to maintain a pressure of less than 50 mbar for a period of time to generate sufficient plasma to affect the surrounding gas (e.g., ambient air) s of the channel 26. For example, the chamber 12 may be shaped and constructed from material which supports maintaining a sub-atmospheric pressure within. In some embodiments, the gas-sealable chamber 12 is configured to maintain sub-atmospheric pressure conditions, especially once the negative pressure pump 18 has been applied to the gas-sealable chamber 12 via connecting conduit 36. In some embodiments, the gas-sealable chamber 12 walls have sufficient structural support to maintain an inner volume within the gas-sealable chamber 12 even under sub-atmospheric and preferable substantially negative pressure conditions relative to the surrounding air.

The chamber body contains gas (e.g., ambient air). The chamber interior region 38 is bound by the chamber walls. The one or more gas-tight utility ports 16 extend through the gas (e.g., ambient air) and into the chamber interior regions. The ports may fluidly connect with a conduit or have an adaptor for connecting a conduit on an inner or outer surface of the port.

Negative pressure pumps are known in the art and are typically designed to generate a low-pressure vacuum through the use of mechanical or electrical means. A negative pressure pump 18 is a device that is designed to generate a low-pressure vacuum through the use of mechanical or electrical means. This pump works by creating areas of low pressure within the chamber 12, which causes fluids or gases to move from within the chamber 12 to outside the chamber 12. The pump can be powered by electric motors, gasoline engines, or compressed air. It typically consists of a housing, a suction port and a discharge port that allows for fluid or gas to flow through the pump. The discharge port would then pass through the one or more gas-tight utility ports 16. In some examples a negative pressure pump 18 or alternatively, a gas supply (e.g., the conduit of the negative pressure or gas supply) may be in fluid communication with the inner volume of gas-sealable chamber 12 via gas-tight utility port 16 which may be positioned on the door 14 or on a chamber gas (e.g., ambient air). The negative pressure or gas source may be configured to sealingly couple to a conduit which passes through the gas-tight utility port or alternatively to the port itself which is in fluid communication with the inner volume of gas-sealable chamber 12. In some embodiments, the gas-tight utility port 16, may comprise a conduit 36 through which negative pressure can be applied from the negative pressure pump 18 to the gas-sealable chamber 12.

The one or more gas-tight utility ports 16 are generally adapted to enable communication or passage between an inner volume of the chamber 12 and a power source 20 or negative pressure or gas source while also substantially isolating an inner pressure within the chamber 12 for example during treatment. For example, the one or more gas-tight utility ports 16 are adapted to allow passage of utility conduits therethrough while substantially limiting gas flow from the outside towards the inside of the chamber 12. Utility conduits include, but not limited, to electrical power lines, vacuum lines, and control lines running between the inside of gas-sealable chamber 12 and the outside of gas-sealable chamber 12 where a negative pressure pump 18, power source 20 and optionally controllers 50 reside. In some embodiments, the gas-tight utility ports 16 are adapted to allow passage of utility conduits therethrough while substantially limiting gas flow between the outside and the inside of the chamber 12.

The gas-tight utility ports 16 may include a or valve, or seal positioned within the port and dimensioned to circumscribe an external circumference of a conduit communicating between an inner volume of the chamber 12 and the outside of the chamber 12. Preferably, the seal or valve ensures that the pressure of the inner volume of the chamber 12 is isolated from the environment. In some embodiments, a one-way valve may be employed to direct gas outwards from the chamber 12. In this embodiment, the port may be further adapted on the outside of the chamber 12 to attach and detach from a conduit in fluid communication with a negative pressure source. This seal may ensure that, during use, ionizable gas present in the working channel 26 does not leak from gas-sealable chamber 12 and the pressure differential between the inside and outside of gas-sealable chamber 12 is achieved and maintained within the gas-sealable chamber 12 for a period of time to allow plasma to be ignited and sustained therein. This ensures that air in the relevant pressure range is available for production of a plasma. The gas-tight utility ports 16 additionally enable a user to have control of the pressure within the gas-sealable chamber 12 via control of the negative pressure pump 18. Thus, the gas-tight utility ports 16 are adapted to hold a vacuum for a prolonged period.

The one or more gas-tight utility ports 16 are typically positioned on a wall or door 14 of gas-sealable chamber 12 and communicate between the inner volume of the chamber body, where sensor or other components are located, and the outside of the gas-sealable chamber 12 where for example, a conduit 36 connecting a negative pressure pump 18, a gas source or a control and monitoring systems that control the electrodes or vacuum applied within the channel 26 (e.g., working channel). Said another way, these utility lines 34 may include gas conduits, electrical power lines, electrical supply conductors, and fluid conduits which may connect a negative pressure pump 18, utility lines 34 (e.g., electrical power lines) and optionally control lines. For example, a utility line may couple to each of the discharge and collecting electrode 24B to the power supply in utility lines 34 such as electrical lines that provide power for the electrodes by connecting between the power source 20 and electrodes. Coupling between the power source and the circumscribing conductive sleeve may be by way of contacting the collecting electrode with an electrically associated portion of the circumscribing conductive sleeve such as a suction port in an endoscope. In some embodiments, the utility lines include gas lines to connect between the interior of the gas-sealable chamber 12 and a gas source.

In an alternative embodiment, gas may intermittently be conveyed from a gas or air source to the gas-sealable chamber 12, in some case replacing the negative pressure pump 18 or in other cases, working in parallel or intermittently with the negative pressure pump. For example, the gas or air may be pumped into the gas-sealable chamber 12 via the gas-tight utility port. Alternatively, the negative pressure pump 18 may apply sub atmospheric conditions within the inner volume of the gas-sealable chamber 12 immediately prior to opening a valve to provide fluid communication between the gas or air source and the inner volume of the gas-sealable chamber 12. In this case, the gas or air flows into the gas-sealable chamber 12 due to a pressure difference.

In some embodiments, in addition to air naturally present in the working channel 26, a periodic supplement of gas flow is supplied to the working channel 26. Examples of suitable gases include but are not limited to air, helium, argon, nitrogen, compressed air, and carbon dioxide. Gas mixtures may be used. Preferably the gas is an inert gas such as Argon or the like, though any gas which is suitable for production of plasma under sub-atmospheric conditions may be chosen. In some embodiments, the gas source may be in fluid communication via a gas line adapted to connect to a gas-supply adapter which is accessible from outside the gas-sealable chamber 12. The gas source may be a single or mixture of gases. In some embodiments, a gas-supply adapter may be configured to sealingly couple to the inside of the gas-sealable chamber 12 via the gas-tight utility ports 16. The gas-supply adapter may also be associated with a valve such that control of flow from outside the gas-sealable chamber 12 is possible. In some embodiments, an automated control unit may be associated with a valve, negative pressure pump 18 or a gas supply pump which periodically or based on a set of factors, enables flow of gas from the gas source into the inner volume of the gas-sealable chamber 12. This may be advantageous in ensuring that air or gas which converts to plasma is continuously passing over the working channel 26. This may be advantageous in playing a role in the drying process of remnants from the earlier reprocessing stages. In some arrangements, door 14 itself may include a valve.

In some embodiments, the method further comprises reintroducing into the channel 26 a fresh volume of air or gas after electrically igniting the gas. In some embodiments, the method further comprises a step of introducing a source of ionizing gas into the channel 26. In a preferred embodiment, the method further comprises reintroducing into the channel 26 a fresh volume of ambient air.

In some embodiments, a pressure relief valve may exist on an external wall of the gas-sealable chamber 12, i.e., accessible from the outside of the gas-sealable chamber 12 and extending through the wall of chamber 12 which allows air or gas to flow in or out of the chamber 12. In some embodiments, the valve functions as a plasma exhaust port extending through said side wall of the chamber 12 and configured to release plasma exhaust or waste. In some embodiments, the exhaust port further comprises a filter configured to filter ozone or other by products of the plasma treatment. One example of a filter may be an active carbon filter.

The valve may be opened before or after activation of a negative pressure pump 18 which is configured to cause a pressure differential between the inside and the outside of the gas-sealable chamber 12. In this embodiment, the gas-sealable chamber 12 is configured for a purging phase. The purging phase may comprise: activating a valve to allow air or gas to flow into the system or into the channel 26 through an inlet; activating a valve to allow air or gas to flow out of the system through an exhaust; and/or allowing the gas or air to be introduced through the valve with or without the activation of a pump (e.g., the vacuum pump). In this case, the pump (e.g., vacuum pump) may be adapted to drive the entry of the gas or air, into the gas-sealable chamber 12. Thus, in some embodiments, the one or more gas-tight utility ports 16 may include conduit 36 such as a gas conduit through which gas can be delivered from a gas supply to the gas-sealable chamber 12 of the surgical scoping device. In this case, the vacuum port could also serve as an exit for excess gas. This may be advantageous in ensuring that gas, and especially ambient air, persistently pass through the gas-sealable chamber 12 to produce a sufficient number of free radicals in the plasma for sterilization.

A flow of gas or ambient air may also be valuable in supporting drying of the working channel 26 of the scoping device. This, in various embodiments, a stage of drying the inner surface of the channel prior to electrically igniting the ambient air is possible. The rate may be for example 1-250 cc per second. This may also be advantageous in ensuring a suitable amount of gas is provided or replaced within the gas-sealable chamber 12 for generating a plasma.

In some embodiments, gas-sealable chamber 12 includes a filter, including using a Hepa or other filtration system. In some embodiments, the filter may be positioned within a port or conduit exiting gas-sealable chamber 12 and play a role when allowing gas or air to exit the chamber, especially post plasma-treatment.

A number of advantages of the present invention are associated with the lengthwise plasma generated within chamber 12 between the elongate discharge electrode and the conductive circumscribing sleeve of the surgical device. For example, a relatively short process is possible compared to methods which involve applying plasma throughout working channel by generating plasma at a focused position and subsequently moving along a working channel. In addition, the present invention avoids the dependance on controlling the gas contents of the working channel which may require an adapter on the end of the working channel, adapted or designed to accommodate each type of scope. In addition, a sub-atmospheric pressure-based plasma allows for additional drying to occur which may benefit the reprocessing process.

Plasma-disinfecting system 10 may be simple to set up as it requires placement of the surgical scope within the gas-sealable chamber 12 and optionally connecting a line to a power source 20 and a line to a negative pressure pump 18 which in some embodiments are preconnected. In another step, positioning one energy transmission element e.g., the elongate discharge electrode 24A within the working channel 26, preferably, in a floating state or contactless state, such that it does not contact the channel walls, and connecting a collecting electrode 24B to a conductive (e.g., metal) circumscribing sleeve which forms another layer of the surgical scope. In another step, sealing the gas-sealable chamber 12 while ensuring a connection to the negative pressure pump 18 and the power source 20 via one or more gas-tight utility ports 16 to obtain a ready-to-ignite state. In a sequential step, activating the plasma generator, whether by a user or controller, to produce a plasma cloud 28 lengthwise along the working channel 26 to generate plasma from the sub-atmospheric air present in the working channel 26.

The disclosed technology may be better understood with respect to the following exemplary embodiments:

1. A method of plasma-disinfecting an inner surface of a working channel of a surgical device, said working channel containing ambient air and having a conductive circumscribing sleeve surrounding the working channel, said method comprising:

i. inserting the surgical device into a gas-sealable chamber;

ii. positioning an elongate discharge electrode within the working channel such that the elongate discharge electrode coaxially spans at least a lengthwise majority of the working channel to define an annular ignition-region within the working channel;

iii. contacting a collecting electrode with a region of the conductive circumscribing sleeve of the surgical device;

iv. gas-sealing the gas-sealable chamber;

v. reducing a pressure of the annular ignition-region containing ambient air to a sub-atmospheric pressure; and vi. electrically igniting the ambient air of the annular ignition-region of the working channel by applying an electrical potential difference sufficient to disinfect the inner surface of the working channel.

2. The method of example 1, wherein applying an electrical potential difference results in a radial and longitudinal plasma cloud.

3. The method of examples 1 to 2, wherein positioning an elongate discharge electrode within the working channel comprises a motor is associated with the elongate discharge electrode and configured to pull to elongate discharge electrode through the working channel.

4. The method of any one of the previous examples, wherein gas-sealing the gas-sealable chamber comprises sealing a gas-sealable door of a chamber, said gas-sealable chamber further having a gas-tight utility port in fluid communication with a negative pressure pump.

5. The method any one of the previous examples, wherein reducing a pressure of the annular ignition-region containing ambient air to sub-atmospheric involves activation of a negative pressure pump outside of the gas-sealable chamber.

6. The method of any one of the previous examples, wherein reducing a pressure of the annular ignition-region comprises reducing the pressure of the gas-sealable chamber to a sub-atmospheric pressure.

7. The method of example 6, wherein reducing a pressure of the annular ignition-region comprises reducing the pressure of the gas-sealable chamber to less than 100 mbar.

8. The method of example 7, wherein reducing a pressure therein to sub-atmospheric is to a pressure of less than 20 mbar.

9. The method any one of the previous examples, wherein igniting the ambient air is by applying an electrical potential difference to the elongate discharge electrode which coaxially spans at least a lengthwise majority of a portion of the working channel.

10. The method any one of the previous examples, wherein igniting the ambient air is by applying an electrical potential difference to the elongate discharge electrode which coaxially spans in a manner which is substantially contactless.

11. The method of any one of the previous examples, wherein applying an electrical potential difference between the elongate discharge electrode and the conductive circumscribing sleeve, said elongate discharge electrode being longitudinally static relative to the working channel for a period of time to disinfect.

12. The method any one of the previous examples, wherein applying an electrical potential difference between the elongate discharge electrode and collecting electrodes for a period of time sufficient to disinfect the inner surface of the working channel.

13. The method any one of the previous examples, wherein applying an electrical potential difference between the elongate discharge electrode and the conductive circumscribing sleeve is along a coaxial length of a working channel of at least 0.75, 1 or 1.5 meter.

14. The method of any one of the previous examples, wherein applying an electrical potential difference between the elongate discharge electrode and the conductive circumscribing sleeve, said elongate discharge electrode having a lengthwise majority being a conducting outer-surface which is uninsulated.

15. The method any one of the previous examples, wherein electrically igniting the ambient air of the annular ignition-region spans at least a lengthwise majority of a proximal half of the working channel or a proximal half of the elongate discharge electrode.

16. The method any one of the previous examples, wherein electrically igniting the ambient air is without relative longitudinal motion between wire and the working channel.

17. The method of any one of the previous examples, wherein sufficient to disinfect is reducing a presence of living microorganisms by at least 3 log CFU per cm^2.

18. The method of example 17, wherein sufficient to disinfect is reducing the presence of living microorganisms is by at least 5 log reduction in CFU per cm^2 on the surface of the channel.

19. The method of example 18, wherein sufficient to disinfect is reducing the presence of living microorganisms by at least 8 log reduction in CFU per cm^2.

20. The method of any one of the previous examples, further comprising a stage of drying the inner surface of the working channel prior to electrically igniting the ambient air.

21. The method of any one of the previous examples, further comprising reintroducing into the working channel a fresh volume of air after electrically igniting the ambient air.

22. The method of any one of the previous examples, further comprising a step of removing ionized gas out of a chamber via a filter.

23. The method of any one of the previous examples, wherein the surgical device further comprises an elevator region and the method further comprises applying to a surgical device tip an additional discharge electrode having a cap shape and adapted to cap an elevator region and electrically igniting an ambient air to form plasma in an area of the elevator region.

24. A disinfection system for plasma-disinfecting an interior surface of a working channel of a surgical device having a conductive circumscribing sleeve surrounding the working channel, said disinfection system comprising:

i. a chamber associated with a negative pressure pump and having a gas-sealable door and one or more gas-tight utility ports;

ii. a plasma generator comprising an elongate discharge electrode and a collecting electrode, each electrically associated with a power source, said plasma generator configured to apply an ionizing electric field radially from the elongate discharge electrode and over a lengthwise majority of the elongate discharge electrode; and iii. a controller said controller configured, when a combination of (i) the chamber, (ii) the plasma generator, and (iii) the working channel is in a ready-to-ignite-plasma state, to electrically ignite at least some ambient air to form plasma, so as to disinfect an inner surface of the surgical device.

25. The disinfection system of example 24, wherein the controller be configured, to electrically ignite at least some ambient air to form plasma, contingent upon a combination of all of the chamber, the plasma generator, and the channel, being in a ready-to-ignite state.

26. The disinfection system of examples 24 or 25, wherein a controller is configured detect that a combination of the chamber, the plasma generator, and the channel are in a ready-to-ignite state prior to electrically igniting at least some ambient air to form plasma.

27. The disinfection system of any one of the example 24 to 26, wherein a ready-to-ignite state requires all of the following: at least a section of the elongate discharge electrode is disposed within the channel of the surgical device so that the elongate discharge electrode coaxially spans at least a lengthwise majority of the channel to define an annular region within the channel; the collecting electrode is in contact with a region of the conductive circumscribing sleeve of the surgical device; the chamber is gas-sealed and the negative pressure pump is activated such that said annular region is maintained at a sub-atmospheric pressure.

28. The disinfection system of any one of the previous examples 24 to 27, wherein the elongate discharge electrode is sized and shaped for longitudinal placement within a working channel and the collecting electrode is adapted to electrically associate with a conductive circumscribing portion of the surgical device.

29. The disinfection system of any one of the previous examples 24 to 28, wherein the elongate discharge electrode has a length of more than 1.5 meters.

30. The disinfection system of any one of the previous examples 24 to 29, wherein the elongate discharge electrode is configured to drive a radial electric field towards a circumscribing conductive circumscribing sleeve of the surgical device.

31. The disinfection system of any one of the previous examples 24 to 30, wherein the elongate discharge electrode further includes a motor configured for advancing the elongate discharge electrode through a length of the working channel.

32. The disinfection system of any one of the previous examples 24 to 31, wherein the collecting electrode is further shaped and sized to function as a hook and positioned on an inner wall of the chamber to secure a portion of the surgical device.

33. The disinfection system of any one of the previous examples 24 to 32, wherein the controller is configured to activate the power source to a power and for a time period sufficient to cause a reduction of contamination on an inner channel surface.

34. The disinfection system of any one of the previous examples 24 to 33, further comprising a cap-shaped discharge electrode, electrically associated with the power source, and configured to cap a surgical device tip.

35. The disinfection system of example 34, wherein the elongate discharge electrode and the cap-shaped discharge electrode are configured for multiple use.

36. The disinfection system of example 34, wherein the elongate discharge electrode and the cap-shaped discharge electrode are configured for single use.

37. The disinfection system of any one of the previous examples 24 to 36, wherein the one or more gas-tight utility ports extend through a wall of the chamber and enable communication between an inner volume of the chamber and a negative pressure pump or gas source.

38. The disinfection system of any one of the previous examples 24 to 37, wherein the one or more gas-tight utility ports and gas-sealable door provide passage while substantially isolating an inner pressure during treatment.

39. The disinfection system of any one of the previous examples 24 to 38, wherein the one or more gas-tight utility ports comprise a seal dimensioned to sealingly circumscribe an external circumference of a conduit communicating between an inner volume of the chamber and outside the chamber.

40. The disinfection system of any one of the previous examples 24 to 39, wherein the chamber is configured for multiple use.

41. The disinfection system of any one of the previous examples 24 to 40, wherein the chamber is configured for single use.

42. The disinfection system of any one of the previous examples 24 to 41, wherein the chamber is flexible but includes structural support to maintain an inner volume surrounding the surgical device despite sub-atmospheric pressure applied.

43. The disinfection system of any one of the previous examples 24 to 42, wherein the chamber further includes a pressure relief valve extending through the wall of the chamber configured to allow air or gas to flow in or out of the chamber.

44. The disinfection system of any one of the previous examples 24 to 43, wherein the chamber further comprises one or more plasma exhaust ports extending through said side wall of the chamber and configured to release plasma exhaust or waste.

45. The disinfection system of any one of the previous examples 24 to 44, the exhaust port further comprises a filter configured to filter ozone or other by products of the plasma treatment.

46. The disinfection system of any one of the previous examples 24 to 46, wherein the power source is an electromagnetic source.

47. The disinfection system of any one of the previous examples 24 to 46, wherein the system further comprises at least one of (i) inserting-means for bringing an elongated discharge electrode into an insert-state relative to the working channel so that the elongate discharge electrode coaxially spans at least a lengthwise majority of the working channel to define an annular region within the working channel; and (ii) detecting means for detecting if the elongated discharge electrode is in said insert-state relative to the working channel.

It should be understood that the use of "and/or" is defined inclusively such that the term "a and/or b" should be read to include the sets: "a and b," "a or b," "a," "b."

The present invention is not limited to what has been particularly shown and described hereinabove. Rather, the scope of the present invention includes both combinations and sub combinations of the various features described hereinabove, as well as variations and modifications thereof that are not in the prior art, which would occur to persons skilled in the art upon reading the foregoing description. Further, the techniques, methods, operations, steps, etc. described or suggested herein can be performed on a living animal or on a non-living simulation, such as on a cadaver, cadaver gastrointestinal tract, simulator (e.g., with the body parts, tissue, etc. being simulated), etc.

Although the operations of some of the disclosed examples are described in a particular, sequential order for convenient presentation, it should be understood that this manner of description encompasses rearrangement, unless a particular ordering is required by specific language set forth above. For example, operations or steps described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are discernible by one of ordinary skill in the art.

BIBLIOGRAPHY

Sakudo A, Yagyu Y, Onodera T. Disinfection and Sterilization Using Plasma Technology: Fundamentals and Future Perspectives for Biological Applications. Int J Mol Sci. 2019 Oct. 21; 20(20):5216.

Van den Berg, D., Asker, D., Awad, T. S. et al. Mechanical deformation of elastomer medical devices can enable microbial surface colonization. Sci Rep 13, 7691 (2023)

The invention claimed is:

1. A disinfection system for plasma-disinfecting an interior surface of a channel of a surgical device having a conductive circumscribing sleeve surrounding the channel, said disinfection system comprising:

i. a pair of spaced-apart electrodes located on opposite sides of a wall of the channel, said spaced-apart electrodes comprising an elongate discharge electrode configured to apply an ionizing electric field radially and over a lengthwise majority of the elongate discharge electrode;

ii. a gas-sealable enclosure having a gas-sealable opening sized to receive the surgical device and one or more gas-tight utility ports spanning a wall of the gas-sealable enclosure, said one or more gas-tight utility ports adapted to:

a. fluidly connect between a negative pressure source on an outside of said enclosure and an end of the channel on the inside; and b. electrically couple between a power source on the outside of said enclosure and the pair of spaced-apart electrodes on the inside of said enclosure; and iii. a controller configured, when a combination of (a) the gas-sealable enclosure, (b) the pair of spaced-apart electrodes, and (c) the channel are in a ready-to-ignite-plasma state, to electrically ignite at least some ambient air to form plasma, so as to disinfect the interior surface of the channel.

2. The disinfection system of claim 1, wherein;

the elongate discharge electrode has a dielectric exterior, and the pair of spaced-apart electrodes located on opposite sides of the channel wall further comprises a collecting electrode adapted to be electrically associated with the conductive circumscribing sleeve of the surgical device.

3. The disinfection system of claim 2, wherein the ready-to-ignite-plasma state requires all of the following:

at least a section of the elongate discharge electrode is disposed within the channel of the surgical device so that the elongate discharge electrode coaxially spans at least a lengthwise majority of the channel to define an annular region within the channel;

the collecting electrode is electrically coupled to the conductive circumscribing sleeve of the surgical device;

the gas-sealable enclosure is gas-sealed, the negative pressure source is connected to one of said one or more gas-tight utility ports and is activated such that said annular region is maintained at a sub-atmospheric pressure.

4. The disinfection system of claim 2, wherein the collecting electrode is adapted to be electrically coupled to a port of an endoscope which is electrically associated with the conductive circumscribing sleeve.

5. The disinfection system of claim 1, wherein the controller is further configured to control the pressure source coupled to the channel to intermittently apply a negative pressure to the channel.

6. The disinfection system of claim 1, wherein the one or more gas-tight utility ports spanning the wall of the gas-sealable enclosure are organized on a single adapter.

7. The disinfection system of claim 1, further comprising a collection chamber associated with the gas-sealable enclosure and configured to receive liquid residue upon application of negative pressure prior to formation of the plasma.

8. The disinfection system of claim 1, wherein the elongate discharge electrode has a length of more than 0.75, 1 or 1.5 meter.

9. The disinfection system of claim 1, wherein the elongate discharge electrode is configured to drive a radial electric field towards the conductive circumscribing sleeve of the surgical device.

10. The disinfection system of claim 1, wherein the elongate discharge electrode further includes a dielectric outer surface.

11. The disinfection system of claim 1, wherein the controller is configured to activate the power source for a time period sufficient to reduce contamination on the interior surface of the channel.

12. The disinfection system of claim 1, further comprising an air inlet for enabling passive entry of air.

13. The disinfection system of claim 1, wherein the gas-sealable enclosure further comprises a pressure relief valve extending through the wall of the gas-sealable enclosure, the pressure relief valve being configured to allow air or gas to flow into or out of the gas-sealable enclosure.

14. The disinfection system of claim 1, wherein the gas-sealable enclosure further comprises one or more plasma exhaust ports extending through the wall of the gas-sealable enclosure, the one or more plasma exhaust ports being configured to release residual waste.

15. The disinfection system of claim 1, further comprising an exhaust port extending through the wall of the gas-sealable enclosure, the exhaust port being associated with a filter or a collection canister, said filter or said collection canister being configured to collect residual by products of the disinfection treatment or of a previous cleaning process.

16. The disinfection system of claim 1, wherein the gas-sealable enclosure is configured for multiple use.

17. The disinfection system of claim 1, wherein the gas-sealable enclosure is configured for a single use.

18. The disinfection system of claim 17, wherein the gas-sealable enclosure is flexible.

19. The disinfection system of claim 1, further comprising:

(i) an inserting-means for at least partially inserting an elongated discharge electrode into the channel so that the elongate discharge electrode coaxially spans at least a lengthwise majority of the channel to define an annular region within the channel; or (ii) a detecting means for detecting if the elongated discharge electrode is at least partially disposed within the channel.

20. The disinfection system of claim 1, wherein the controller is configured to electrically ignite at least some of the ambient air to form the plasma directly within the surgical device.

\* \* \* \* \*